United States Patent
Liu et al.

(10) Patent No.: US 12,318,398 B2
(45) Date of Patent: Jun. 3, 2025

(54) MST1 KINASE INHIBITOR AND USE THEREOF

(71) Applicant: HEFEI INSTITUTES OF PHYSICAL SCIENCE, CHINESE ACADEMY OF SCIENCES, Anhui (CN)

(72) Inventors: Qingsong Liu, Anhui (CN); Jing Liu, Anhui (CN); Yun Wu, Anhui (CN); Wenliang Wang, Anhui (CN); Beilei Wang, Anhui (CN); ZiPing Qi, Anhui (CN); Junjie Wang, Anhui (CN); Wenchao Wang, Anhui (CN); Shuang Qi, Anhui (CN); Li Wang, Anhui (CN)

(73) Assignee: Tarapeutics Science Inc., Anhui (CN)

( * ) Notice: Subject to any disclaimer, the term of this patent is extended or adjusted under 35 U.S.C. 154(b) by 1092 days.

(21) Appl. No.: 17/283,646

(22) PCT Filed: Oct. 9, 2019

(86) PCT No.: PCT/CN2019/110048
§ 371 (c)(1),
(2) Date: Apr. 8, 2021

(87) PCT Pub. No.: WO2020/073906
PCT Pub. Date: Apr. 16, 2020

(65) Prior Publication Data
US 2021/0346406 A1    Nov. 11, 2021

(30) Foreign Application Priority Data
Oct. 12, 2018   (CN) .......................... 201811190756.1

(51) Int. Cl.
| | |
|---|---|
| *A61K 31/635* | (2006.01) |
| *A61K 31/519* | (2006.01) |
| *A61K 31/5377* | (2006.01) |
| *A61P 1/16* | (2006.01) |
| *A61P 3/10* | (2006.01) |
| *C07D 475/00* | (2006.01) |
| *C07D 475/12* | (2006.01) |

(52) U.S. Cl.
CPC .......... *A61K 31/635* (2013.01); *A61K 31/519* (2013.01); *A61K 31/5377* (2013.01); *A61P 1/16* (2018.01); *A61P 3/10* (2018.01); *C07D 475/00* (2013.01); *C07D 475/12* (2013.01)

(58) Field of Classification Search
CPC ................ A61K 31/635; A61K 31/519; A61K 31/5377; A61P 1/16; A61P 3/10; A61P 1/00; A61P 5/14; A61P 5/38; A61P 7/00; A61P 7/06; A61P 9/00; A61P 11/06; A61P 15/14; A61P 17/00; A61P 19/02; A61P 19/08; A61P 21/04; A61P 27/02; A61P 29/00; A61P 37/02; A61P 37/06; A61P 1/04; C07D 475/00; C07D 475/12
See application file for complete search history.

(56) References Cited

U.S. PATENT DOCUMENTS

2013/0225593 A1 *   8/2013   Eickmeier ............ C07D 491/20

FOREIGN PATENT DOCUMENTS

| | | | |
|---|---|---|---|
| CN | 103429582 A | 12/2013 | |
| CN | 105801582 | * 7/2016 | ........... C07D 475/00 |
| CN | 105801582 A | 7/2016 | |
| CN | 105939607 A | 9/2016 | |
| CN | 107151250 A | 9/2017 | |
| WO | 03/020722 A1 | 3/2003 | |

(Continued)

OTHER PUBLICATIONS

El-Haj BM, Ahmed SBM, Garawi MA, Ali HS. Linking Aromatic Hydroxy Metabolic Functionalization of Drug Molecules to Structure and Pharmacologic Activity. Molecules, 2018, 23(9):2119 (Year: 2018).*
CAS Registry No. 7664-41-7; entered STN Nov. 16, 1984 (Year: 1984).*
Supplementary European Search Report dated May 27, 2022 received in EP Application No. 19870543.6, 10 pages.
International Search Report dated Dec. 27, 2019 issued in PCT/CN2019/110048.
Chinese Office Action dated Mar. 29, 2021 issued in CN 2019109143342.

(Continued)

*Primary Examiner* — Alicia L Otton
*Assistant Examiner* — David M Shim
(74) *Attorney, Agent, or Firm* — Scully, Scott, Murphy & Presser, P.C.

(57) ABSTRACT

Disclosed is a kinase inhibitor, comprising a compound of formula (I) or a pharmaceutically acceptable salt, solvate, ester, acid, metabolite, or prodrug thereof. Also disclosed are a pharmaceutical composition comprising the kinase inhibitor and uses and methods for inhibiting the activity of one or more tyrosine kinases selected from MST1 and a mutant thereof in a cell or subject and for preventing or treating a disease related to MST1 or a mutant thereof in a subject by using the compound or composition.

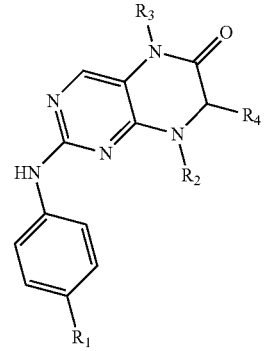

Formula (I)

7 Claims, 3 Drawing Sheets

(56) References Cited

FOREIGN PATENT DOCUMENTS

WO     2008050096 A1     5/2008
WO     2014145909 A2     9/2014

OTHER PUBLICATIONS

Anand, R. et al., "Toward the Development of a Potent and Selective Organoruthenium Mammalian Sterile 20 Kinase Inhibitor", Journal of Medicinal Chemistry (2009), vol. 52, No. 6, pp. 1602-1611.

Ardestani, A. et al., "MST1 is a key regulator of beta cell apoptosis and dysfunction in diabetes", Nature Medicine (Apr. 2014), vol. 20, No. 4, pp. 385-397.

Davis, M.E. et al., "Cyclodextrin-Based Pharmaceutics: Past, Present and Future", Nature Reviews (Dec. 2004), vol. 3, pp. 1023-1035.

Fan, F. et al., "Pharmacological targeting of kinases MST1 and MST2 augments tissue repair and regeneration", Science Translation Medicine (Aug. 17, 2016), vol. 8, Issue 352, 352ra108, pp. 1-14.

\* cited by examiner

MST1 KINASE INHIBITOR AND USE THEREOF

FIELD OF THE INVENTION

The invention relates to a compound that can be used as an inhibitor of mammalian Ste20-like kinase 1 (MST1), and a composition comprising the compound and use thereof.

BACKGROUND OF THE INVENTION

MST1 kinase has a variety of biological functions such as regulating cell proliferation, growth, apoptosis and organ size. Studies have found that the abnormal expression of MST1 protein is closely related to major diseases such as tumor, nervous system disease, heart disease, autoimmune disease, and diabetes. Therefore, MST1 can be used as a potential target for diagnosis, prognosis and treatment. Mammalian sterile 20-like kinase 1 (MST1) gene was cloned from the lymphatic cDNA library by PCR in 1995 when studying human homologue of *Saccharomyces cerevisiae* Ste20, and its encoding product had similar structure and function as yeast Ste20, and thus was named as MST1. The MST1 kinase belongs to mammalian Ste20 related kinases. As a prototype, MST1 also has three paralogs, i.e., MST2, MST3 and MST4.

Diabetes is a metabolic disease characterized by hyperglycemia. It is the world's third most serious chronic disease that harms human health. Hyperglycemia is caused by a defect or impaired biological action of insulin secretion, or both. Among them, about 5% of the patients have type 1 diabetes (also known as insulin-dependent diabetes) with severely insufficient insulin within the body, while about 95% of the patients have type 2 diabetes with reduced insulin sensitivity and impaired insulin secretion. Insulin is secreted by pancreatic β cells. The loss of the number and function of pancreatic β-cells is the pathological basis of most diabetes. In type 1 diabetes, due to the combination of genetic and environmental factors, the β cells are recognized by the autoimmune system as foreign cells, and are attacked by the autoimmune system, leading to the destruction of β cell population. Therefore, the patients must rely on exogenous administration of insulin to maintain glucose homeostasis. Type 2 diabetes is mainly caused by insulin resistance (IR) and pancreatic β-cell dysfunction. Insulin resistance will hinder the processing of glucose and metabolism of fat in insulin sensitive tissues, especially muscle, liver and adipose tissues. In order to compensate for such an insulin resistance, pancreatic β-cells can increase the secretion of insulin to maintain a proper production and utilization of glucose. However, as the function of pancreatic β-cells gradually declines, insulin secretion will eventually become insufficient.

There are many therapeutic drugs for diabetes, but the existing drugs have certain limitations. There is an urgent need in clinic for new anti-diabetic drugs with a new mechanism of action. Pancreatic β-cells are the core participants in the pathogenesis of type 1 and type 2 diabetes, and it may be an effective therapeutic strategy to improve the function of pancreatic β-cells to maintain glucose homeostasis. Studies have found that MST1 plays an important regulatory role in the process of death or apoptosis of pancreatic β cell (Ardestani A, et al., MST1 is a key regulator of beta cell apoptosis and dysfunction in diabetes. *Nat Med.* 2014, 20, 385-397), and can be used as a potential new target for the development of drugs for the treatment of diabetes.

In addition to diabetes, MST1 inhibitors also play an important role in the repair of liver damage and the treatment of hepatitis.

The development of drugs targeting MST1 kinase is still at the initial stage, and so far, no drugs have been approved for marketing. There are only few drugs that are immediately before clinical development. Among them, the patent CN201280011749.5 in 2012 is the earliest reported patent, and XMU-MP-1 is the most representative one (Fan F, et al., Pharmacological targeting of kinases MST1 and MST2 augments tissue repair and regeneration. *Sci. Transl. Med.* 2016, 8, 352ra108). The inhibitor fails to achieve selectivity between MST1 and MST2, and showed comparable inhibitory activity ($IC_{50}$ was 71 nM and 38 nM, respectively). It also has a significant inhibitory effect on certain kinases of the same family (MAP3K2, TAOK, etc.). In addition, as the catalytic regions of most kinases are highly conserved and have a high similarity, other related kinases such as PIK3CG, AURKA, etc. will also be inhibited accordingly. Organometallic ruthenium MST1 inhibitor 9E (Anand R, et al., Toward the Development of a Potent and Selective Organoruthenium Mammalian Sterile 20 Kinase Inhibitor. *J. Med. Chem.* 2009, 52, 1602-1611) is a multi-target inhibitor reported in 2009 and has an inhibitory activity against MST1 with an $IC_{50}$ of 45 nM. Although it has achieved relatively good selectivity (8-25 times) in the same family, it has not shown selectivity in other related kinases PIM1 and GSK3β (with an $IC_{50}$ of 0.6 nM and 13 nM, respectively).

SUMMARY OF THE INVENTION

The invention relates to a compound that can be used to inhibit MST1 kinase. One embodiment of the invention relates to a compound of Formula (I) or a pharmaceutically acceptable salt, solvate, ester, acid, metabolite or prodrug thereof,

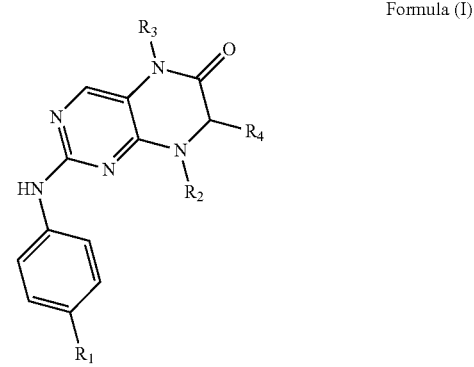

Formula (I)

wherein,
$R_1$ is selected from

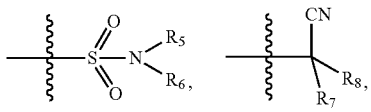

and C3-C6 heterocycloalkyl (e.g., piperazinyl, morpholinyl, etc., and the heterocycloalkyl may be optionally substituted with C1-C6 alkyl);

$R_2$ and $R_3$ are each independently selected from C1-C6 alkyl, preferably C1-C3 alkyl, more preferably methyl;

$R_4$ is selected from C1-C6 alkyl, C3-C6 cycloalkyl, C4-C8 cycloalkylalkyl, C2-C6 spirocycloalkyl, and aryl (e.g., phenyl and naphthyl, etc.) optionally independently substituted with 1-3 $R_9$, aryl C1-C6 alkyl (e.g., phenylmethyl, etc.) optionally independently substituted with 1-3 $R_9$ and heteroaryl (e.g., thienyl, etc.) optionally independently substituted with 1-3 $R_9$;

$R_5$ and $R_6$ are each independently selected from hydrogen, C1-C6 alkyl, C3-C6 cycloalkyl, C4-C8 cycloalkylalkyl, C3-C6 heterocycloalkyl, hydroxyl C1-C6 alkyl, C1-C6 alkylamino, C1-C6 haloalkyl, C1-C6 alkylamino C1-C6 alkyl, C1-C6 alkoxy C1-C6 alkyl, and C3-C6 heterocyclyl C1-C6 alkyl (the heterocyclyl is selected from e.g., piperidyl, tetrahydropyranyl, etc.);

$R_7$ and $R_8$ are each independently selected from C1-C6 alkyl, or $R_7$, $R_8$ together with the carbon atom attached thereto form C3-C6 cycloalkyl or C3-C6 heterocyclyl (e.g., tetrahydropyranyl, etc.);

$R_9$ is selected from halogen, C1-C6 alkyl, C1-C6 alkoxy, and C1-C6 haloalkyl.

A preferred embodiment encompasses the compound of the invention, which is a compound of Formula (Ia) or a pharmaceutically acceptable salt, solvate, ester, acid, metabolite or prodrug thereof,

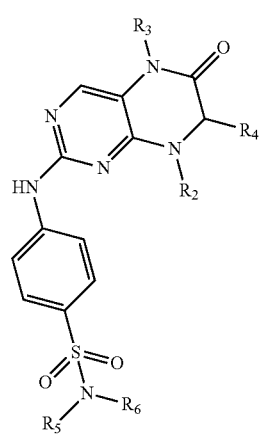

Formula (Ia)

wherein $R_2$, $R_3$, $R_4$, $R_5$ and $R_6$ are defined as above.

More preferably, in the compound of Formula (Ia), $R_2$ and $R_3$ are methyl, $R_4$ is selected from C1-C6 alkyl, C2-C6 spirocycloalkyl, and phenyl optionally substituted with 1-3 halogen or thienyl optionally substituted with 1-3 halogen, $R_5$ and $R_6$ are each hydrogen.

The invention also relates to a pharmaceutical composition comprising the compound of the invention and a pharmaceutically acceptable excipient.

In a further aspect, the embodiment of the invention encompasses a method and use for the inhibition of MST1 kinase by using the compound or pharmaceutical composition of the invention.

Another embodiment of the invention encompasses a method and use for the treatment or prevention of diabetes by using the compound or pharmaceutical composition of the invention, particularly a method and use for the treatment or prevention of type 1 diabetes and type 2 diabetes.

In other embodiments, the invention encompasses a method and use for the treatment or prevention of inflammatory or autoimmune diseases by using the compound or pharmaceutical composition of the invention.

The MST1 inhibitor contemplated in the invention plays an important impair role in the acute liver injury repair model. In the treatment of diabetes, the inhibitor of the invention has a certain inhibitory effect on the apoptosis of pancreatic β-cells mediated by MST1 related signaling pathways, and has a certain activatory effect on the transcription factor PDX1 related to insulin secretion, indicating that the MST1 inhibitor also has a certain therapeutic effect in diabetes.

DETAILED DESCRIPTION OF THE INVENTION

Terminology

Figure 1A:
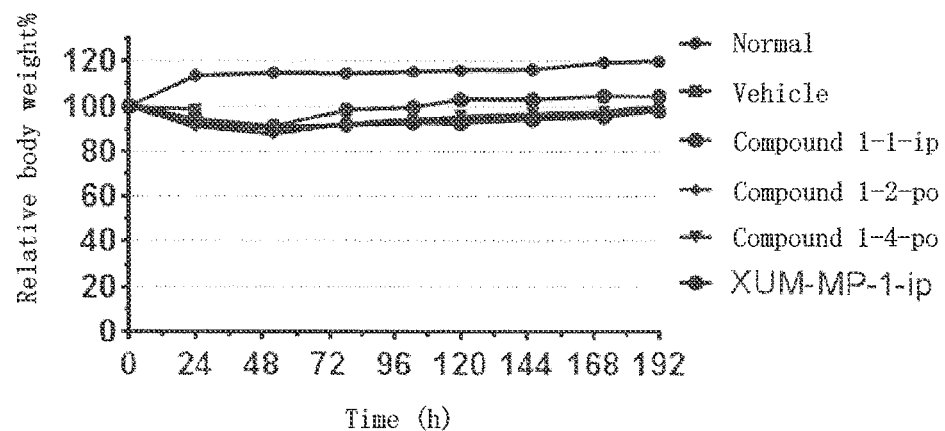
FIG. 1a shows the change of body weight of mice in the normal group, the vehicle group and the treatment group in the liver injury repair model.
Figure 1B:
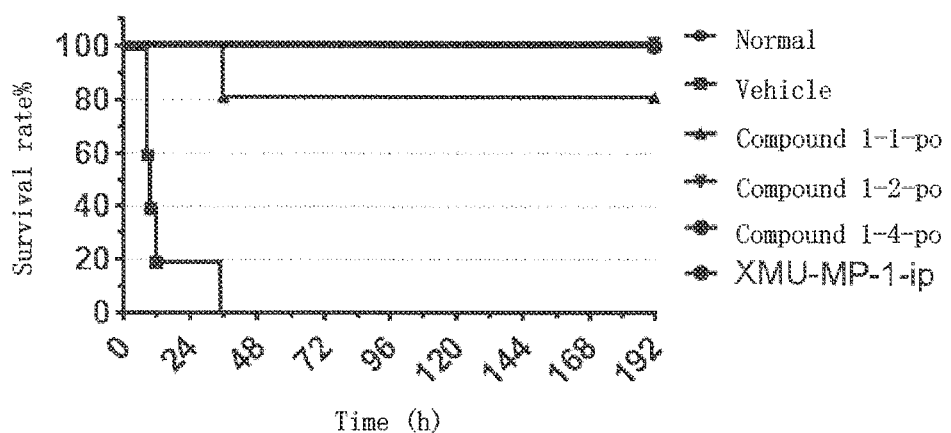
FIG. 1b shows the survival rate of mice in the normal group, the vehicle group and the treatment group in the liver injury repair model.

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferably an alkyl having 1 to 8 carbon atoms, and more preferably a "lower alkyl" having 1 to 6 carbon atoms, and even more preferably an alkyl having 1 to 4 carbon atoms. Typical alkyl groups include, but are not limited to, methyl, ethyl, propyl, butyl, pentyl, hexyl, and the like. It should be understood that the "alkyl" mentioned herein includes all possible configurations and conformations of the alkyl group. For example, the "propyl" mentioned herein includes n-propyl and isopropyl, "butyl" includes n-butyl, isobutyl, and tert-butyl, "pentyl" includes n-pentyl, isopentyl, neopentyl, tert-pentyl, and pent-3-yl.

The term "alkoxy" refers to an —O-alkyl group, where the alkyl is as defined herein. Typical alkoxy groups include, but are not limited to, methoxy, ethoxy, propoxy, butoxy, pentyloxy, hexyloxy, and the like.

The term "alkoxyalkyl" refers to an alkyl radical, as defined herein, substituted with an alkoxy group, as defined herein.

The term "cycloalkyl" refers to a monocyclic or polycyclic radical that contains only carbon and hydrogen. Cycloalkyl groups include groups having from 3 to 12 ring atoms. Depending on the structure, a cycloalkyl group can be a monoradical or a diradical (e.g., an cycloalkylene group). In the invention, the cycloalkyl group is preferably a cycloalkyl having 3 to 8 carbon atoms, and more preferably a "lower cycloalkyl" having 3 to 6 carbon atoms. Examples of cycloalkyl groups include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl.

The term "alkyl(cycloalkyl)" or "cycloalkylalkyl" refers to an alkyl radical, as defined herein, substituted with a cycloalkyl group, as defined herein. Non-limiting cycloalkylalkyl groups include cyclopropylmethyl, cyclobutylmethyl, cyclopentylmethyl, cyclohexylmethyl, and the like.

The term "aromatic" refers to a planar ring having a delocalized π-electron system containing $4n+2\pi$ electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed from five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furyl, benzofuranyl, benzothiophenyl, benzothiazolyl, benzoxazolyl, quinazolinyl, naphthyridinyl, furopyridinyl, and the like.

The term "alkyl(aryl)" or "aralkyl" refers to an alkyl radical, as defined herein, substituted with an aryl group, as defined herein. Non-limiting alkyl(aryl) groups include benzyl, phenethyl, and the like.

The term "alkyl(heteroaryl)" or "heteroarylalkyl" refers to an alkyl radical, as defined herein, substituted with a heteroaryl group, as defined herein.

As used herein, the term "heteroalkyl" refers to an alkyl radical, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

As used herein, the term "heterocycloalkyl" or "heterocyclyl" refers to a non-aromatic ring wherein one or more atoms forming the ring is a heteroatom selected from nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heterocycloalkyl)" or "heterocycloalkylalkyl" refers to an alkyl radical, as defined herein, substituted with a heterocycloalkyl group, as defined herein.

The term "alkoxy(heterocycloalkyl)" or "heterocycloalkylalkoxy" refers to an alkoxy radical, as defined herein, substituted with a heterocycloalkyl group, as defined herein.

The term "halo" or "halogen" refers to fluoro, chloro, bromo and iodo.

The terms "haloalkyl", "haloalkoxy" and "haloheteroalkyl" include alkyl, alkoxy or heteroalkyl structures in which at least one hydrogen is replaced with a halogen atom. In certain embodiments in which two or more hydrogen atoms are replaced with halogen atoms, the halogen atoms are the same or different as one another.

The term "hydroxy" refers to an —OH group.

The term "amide" or "amido" refers to —NR—CO—R', wherein R and R' are independently hydrogen or alkyl.

The term "alkylamino" refers to an amino substituent which is further substituted with one or two alkyl groups, specifically refers to the group —NRR', wherein R and R' are each independently selected from the group consisting of hydrogen or lower alkyl, with the proviso that —NRR' is not —NH$_2$. "Alkylamino" includes groups of compounds in which the nitrogen atom of —NH$_2$ is attached to at least one alkyl group. Examples of alkylamino groups include, but are not limited to, methylamino, ethylamino, and the like. "Dialkylamino" includes groups in which the nitrogen atom of —NH$_2$ is attached to at least two other alkyl groups. Examples of dialkylamino groups include, but are not limited to, dimethylamino, diethylamino, and the like.

The term "cycloalkylamino" refers to an amino substituent further substituted with one or two cycloalkyl groups as defined herein.

The term "heterocycloalkylamino" refers to an amino radical, as defined herein, substituted with a heterocycloalkyl group, as defined herein.

The term "alkylaminoalkyl" refers to an alkyl radical, as defined herein, substituted with an alkylamino group, as defined herein.

The term "aminoalkyl" refers to an alkyl substituent further substituted with one or more amino groups.

The term "aminoalkoxy" refers to an alkoxy substituent further substituted with one or more amino groups.

The term "hydroxyalkyl" or "hydroxylalkyl" refers to an alkyl substituent further substituted with one or more hydroxy groups.

The term "cyanoalkyl" refers to an alkyl substituent further substituted with one or more cyano groups.

The term "acyl" refers to a monovalent atomic radical remaining after removal of the hydroxyl group from an organic or inorganic oxyacid, represented by a general formula of R-M(O)—, wherein M is usually C.

The term "carbonyl" is an organic functional group (C=O) formed by carbon atom and oxygen atom through a double bond linkage.

The term "alkanoyl" or "alkylcarbonyl" refers to a carbonyl group further substituted with an alkyl group. Typical alkanoyl groups include, but are not limited to, acetyl, propionyl, butyryl, valeryl, hexanoyl and the like.

The term "arylcarbonyl" refers to a carbonyl radical, as defined herein, substituted with an aryl group, as defined herein.

The term "alkoxycarbonyl" refers to a carbonyl radical further substituted with an alkoxy group.

The term "heterocycloalkylcarbonyl" refers to a carbonyl radical further substituted with a heterocycloalkyl group.

The terms "alkylaminocarbonyl", "cycloalkylaminocarbonyl", "arylaminocarbonyl", "aralkylaminocarbonyl", and "heteroarylaminocarbonyl" refer to a carbonyl radical, as defined herein, substituted with an alkylamino, cycloalkylamino, arylamino, aralkylamino, or heteroarylamino group, as defined herein, respectively.

The term "alkylcarbonylalkyl" or "alkanoylalkyl" refers to an alkyl radical further substituted with an alkylcarbonyl group.

The term "alkylcarbonylalkoxy" or "alkanoylalkoxy" refers to an alkoxy radical further substituted with an alkylcarbonyl group.

The term "heterocycloalkylcarbonylalkyl" refers to an alkyl radical further substituted with a heterocycloalkylcarbonyl group.

The term "sulfuryl" or "sulfonyl" refers to a functional group after the sulfonic acid loses the hydroxyl group, and specifically refers to a —S(=O)$_2$— group.

The term "sulfoxide" or "sulfinyl" refers to —S(=O)—.

The term "aminosulfuryl" or "aminosulfonyl" refers to a —S(=O)$_2$—NH$_2$ group.

The term "alkylsulfoxide" or "alkylsulfinyl" refers to alkyl-S(=O)—.

The term "alkylsulfuryl" or "alkylsulfonyl" refers to —S(=O)$_2$—R, where R is an alkyl group.

The term "alkylaminosulfuryl" refers to a sulfuryl radical, as defined herein, substituted with an alkylamino group, as defined herein.

The term "alkylsulfurylamino" or "cycloalkylsulfurylamino" refers to an amino radical, as defined herein, substituted with an alkylsulfuryl group or a cycloalkylsulfuryl group, as defined herein.

The terms "cycloalkylsulfuryl" and "cycloalkylsulfonyl" refer to —S(=O)$_2$—R, where R is a cycloalkyl group.

The terms "alkylsulfonamido" and "cycloalkylsulfonamido" refer to —NH—S(=O)$_2$—R, where R is an alkyl group and a cycloalkyl group, respectively.

The term "optionally" means that one or more events described hereinafter may or may not occur, and include both the event(s) that may occur and the event(s) that may not occur. The term "optionally substituted" or "substituted" refers to that the mentioned group may be substituted with one or more additional groups which are each independently selected from alkyl, cycloalkyl, aryl, heteroaryl, heterocyclyl, hydroxy, alkoxy, cyano, halo, amide, nitro, haloalkyl, amino, methylsulfonyl, alkylcarbonyl, alkoxy carbonyl, heteroarylalkyl, heterocycloalkylalkyl, aminoacyl, amino protecting group, etc., wherein, the amino protecting group is preferably selected from the group consisting of pivaloyl, tert-butoxycarbonyl, benzyloxycarbonyl, 9-fluorenylmethoxycarbonyl, benzyl, p-methoxybenzyl, allyloxycarbonyl, trifluoroacetyl, and the like.

The term "tyrosine protein kinase (TPK)" as used herein is a type of kinase that catalyzes the transfer of γ-phosphate from ATP to tyrosine residues of a protein, catalyzes phosphorylation of tyrosine residues of various substrate proteins, and plays an important role in cell growth, proliferation, and differentiation.

The term "inhibit", "inhibitory", or "inhibitor" of a kinase, as used herein, refers to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may cause specific structural alterations. For example, cytochrome P450 catalyzes a variety of oxidation and reduction reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidation processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In certain embodiments, the target protein is mammalian Ste20-like kinase 1 (MST1).

As used herein, IC$_{50}$ refers to an amount, concentration or dosage of a particular test compound that achieves a 50% inhibition of a maximal response, in an assay that measures such response.

As used herein, EC$_{50}$ refers to a dosage, concentration or amount of a test compound that elicits a dose-dependent response at 50% of maximal expression of a particular response that is induced, provoked or potentiated by the particular test compound.

As used herein, $GI_{50}$ refers to a drug concentration required for 50% growth inhibition of cells, i.e., a drug concentration at which the growth of 50% cells (such as cancer cells) can be inhibited or controlled by the drug.

Method of Use

This invention encompasses a method of inhibiting MST1, which comprises contacting MST1 (in vitro or in vivo) with an effective amount of a compound of the invention.

Another embodiment encompasses a method of suppressing immune response in a patient (e.g., a human), which comprises administering to the patient an effective amount of a compound of the invention.

Another embodiment encompasses a method of treating, or preventing an autoimmune or inflammatory disease or disorder, which comprises administering to a patient in need thereof a therapeutically or prophylactically effective amount of a compound of the invention. Examples of diseases and disorders include autoimmune achlorhydria, Addison's Disease, ankylosing spondylitis, anti-phospholipid syndrome, asthma (e.g., bronchial asthma), atopic dermatitis, autoimmune atrophic gastritis, Behcet's disease, Celiac Disease, Crohn's Disease, Cushing's Syndrome, dermatomyositis, Goodpasture's Syndrome, graft-vs-host disease, Grave's Disease, Hashimoto's thyroiditis, hepatitis (e.g., Inflammation and alcohol-induced), idiopathic adrenal atrophy, idiopathic thrombocytopenia, Kawasaki syndrome, Lambert-Eaton Syndrome, lupus erythematosus, multiple sclerosis, myasthenia gravis, pemphigoid, pernicious anemia, pollinosis, polyarteritis nodosa, primary polychondritis, rheumatoid arthritis, Schmidt's Syndrome, psoriatic arthritis, Raynaud's disease, Reiter's Syndrome, relapsing polychondritis, rheumatoid arthritis, Schmidt's Syndrome, scleroderma, Sjogren's Syndrome, sympathetic ophthalmia, Takayasu's Arteritis, temporal arteritis, thyrotoxicosis, transplant rejection (e.g., of organ, cell or bone marrow), diabetes, ulcerative colitis, uveitis, and Wegener's granulomatosis.

Another embodiment encompasses the treatment or prevention of diabetes, particularly type 1 diabetes or type 2 diabetes.

Another embodiment encompasses the treatment or prevention of hepatitis and liver damage, especially the repair of acute liver damage.

The amount, route of administration and dosing schedule of a compound will depend upon factors such as the specific indication to be treated or prevented, and the age, sex and condition of the patient. The roles played by such factors are well known in the art, and may be accommodated by routine experimentation. In a particular embodiment, a compound of the invention is administered to a human patient in an amount of about 1-50, 1-25, or 2.5-15, or 5-10 mg/kg.

Compounds of the invention can be administered in combination with other immunosuppressant or anti-inflammatory drugs. The drugs can be administered at the same or at different times.

Examples of immunosuppressants include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept. Additional examples include inosine monophosphate dehydrogenase inhibitors, such as mycophenolate mofetil (CellCept®) and mycophenolic acid (Myfortic®).

Examples of anti-inflammatory drugs include glucocorticoids and NSAIDs.

Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAIDs include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Pharmaceutical Compositions

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, the oral administration of a compound susceptible to degradation in the stomach may be achieved using an enteric coating. Similarly, a formulation may contain ingredients that facilitate delivery of the active ingredient(s) to the site of action. For example, compounds may be administered in liposomal formulations in order to protect them from degradative enzymes, facilitate transport in circulatory system, and effect their delivery across cell membranes.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin, β-cyclodextrin), Captisol®, and Encapsin™ (see, e.g., Davis and Brewster, *Nat. Rev. Drug Disc.* (2004) 3: 1023-1034), Labrasol®, Labrafil®, Labrafac®, Cremafor, and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO: cornoil).

The composition, shape, and type of a dosage form will typically vary depending with use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. How to account for such differences will be apparent to those skilled in the art. See, e.g., Remington's Pharmaceutical Sciences, 18th ed., Mack Publishing, Easton PA (1990).

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton PA (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facilitate rapid dissolution. Lubricants may also be incorporated to facilitate the manufacture of dosage forms (e.g., tablets).

Parenteral dosage forms can be administered to patients by various routes including subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Compound of the Invention

The invention relates to a compound that can be used to inhibit MST1 kinase. One embodiment of the invention relates to a compound of Formula (I) or a pharmaceutically acceptable salt, solvate, ester, acid, metabolite or prodrug thereof,

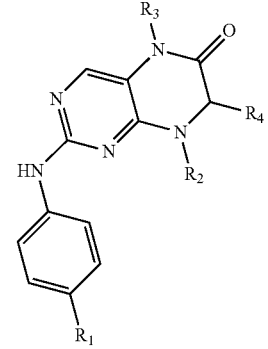

Formula (I)

wherein,
$R_1$ is selected from

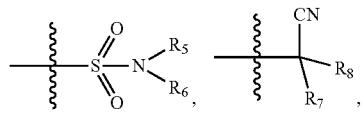

and C3-C6 heterocycloalkyl (e.g., piperazinyl, morpholinyl, etc., and the heterocycloalkyl may be optionally substituted with C1-C6 alkyl);

$R_2$ and $R_3$ are each independently selected from C1-C6 alkyl, preferably C1-C3 alkyl, more preferably methyl;

$R_4$ is selected from C1-C6 alkyl, C3-C6 cycloalkyl, C4-C8 cycloalkyl alkyl, C2-C6 spirocycloalkyl, and aryl (e.g., phenyl and naphthyl, etc.) optionally independently substituted with 1-3 $R_9$, aryl C1-C6 alkyl (e.g., phenylmethyl, etc.) optionally independently substituted with 1-3 $R_9$ and heteroaryl (e.g., thienyl, etc.) optionally independently substituted with 1-3 $R_9$;

$R_5$ and $R_6$ are each independently selected from hydrogen, C1-C6 alkyl, C3-C6 cycloalkyl, C4-C8 cycloalkyl alkyl, C3-C6 heterocycloalkyl, hydroxyl C1-C6 alkyl, C1-C6 alkylamino, C1-C6 haloalkyl, C1-C6 alkylamino C1-C6 alkyl, C1-C6 alkoxy C1-C6 alkyl, and C3-C6 heterocyclyl C1-C6 alkyl (the heterocyclyl is selected from e.g., piperidyl, tetrahydropyranyl, etc.);

$R_7$ and $R_8$ are each independently selected from C1-C6 alkyl, or $R_7$, $R_8$ together with the carbon atom attached thereto form C3-C6 cycloalkyl or C3-C6 heterocyclyl (e.g., tetrahydropyranyl, etc.);

$R_9$ is selected from halogen (preferably fluorine and chlorine, more preferably fluorine), C1-C6 alkyl (preferably methyl), C1-C6 alkoxy, and C1-C6 haloalkyl (preferably trifluoromethyl).

A preferred embodiment encompasses a compound of the invention, which is a compound of Formula (Ia) or a pharmaceutically acceptable salt, solvate, ester, acid, metabolite or prodrug thereof,

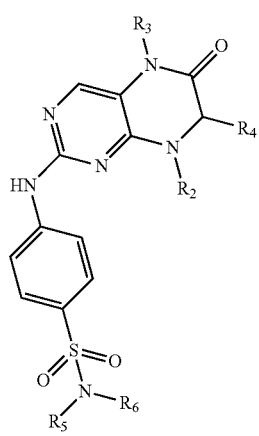

Formula (Ia)

wherein $R_2$, $R_3$, $R_4$, $R_5$ and $R_6$ are defined as above.

More preferably, in the compound of Formula (Ia), $R_2$ and $R_3$ are methyl, $R_4$ is selected from C1-C6 alkyl, C2-C6 spirocycloalkyl, and phenyl optionally independently substituted with 1-3 $R_9$ or thienyl optionally independently substituted with 1-3 $R_9$, $R_5$ and $R_6$ are each hydrogen, wherein $R_9$ is selected from halogen, C1-C6 alkyl, and C1-C6 haloalkyl. More preferably, $R_9$ is selected from fluorine, methyl and trifluoromethyl.

In a preferred embodiment, the kinase inhibitor of the invention includes the following compounds or a pharmaceutically acceptable salt, solvate, ester, acid, metabolite or prodrug thereof:

| Example No. | Structure of Compound |
|---|---|
| 1 | 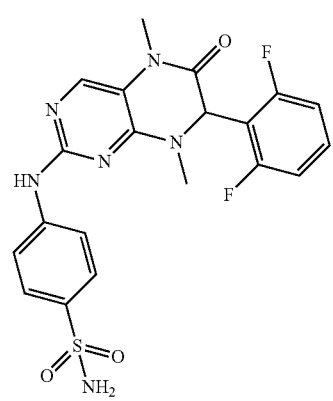 |

| Example No. | Structure of Compound |
|---|---|
| 2 | |
| 3 | |
| 4 | |
| 5 | |

-continued

| Example No. | Structure of Compound |
|---|---|
| 6 | (structure) |
| 7 | (structure) |
| 8 | (structure) |
| 9 | (structure) |
| 10 | (structure) |
| 11 | (structure) |
| 12 | (structure) |

-continued

| Example No. | Structure of Compound |
|---|---|
| 13 | |
| 14 | |
| 15 | |
| 16 | |

-continued

| Example No. | Structure of Compound |
|---|---|
| 17 | |
| 18 | |
| 19 | |
| 20 | |

-continued
| Example No. | Structure of Compound |
|---|---|
| 21 | |
| 22 | |
| 23 | |
| 24 | |
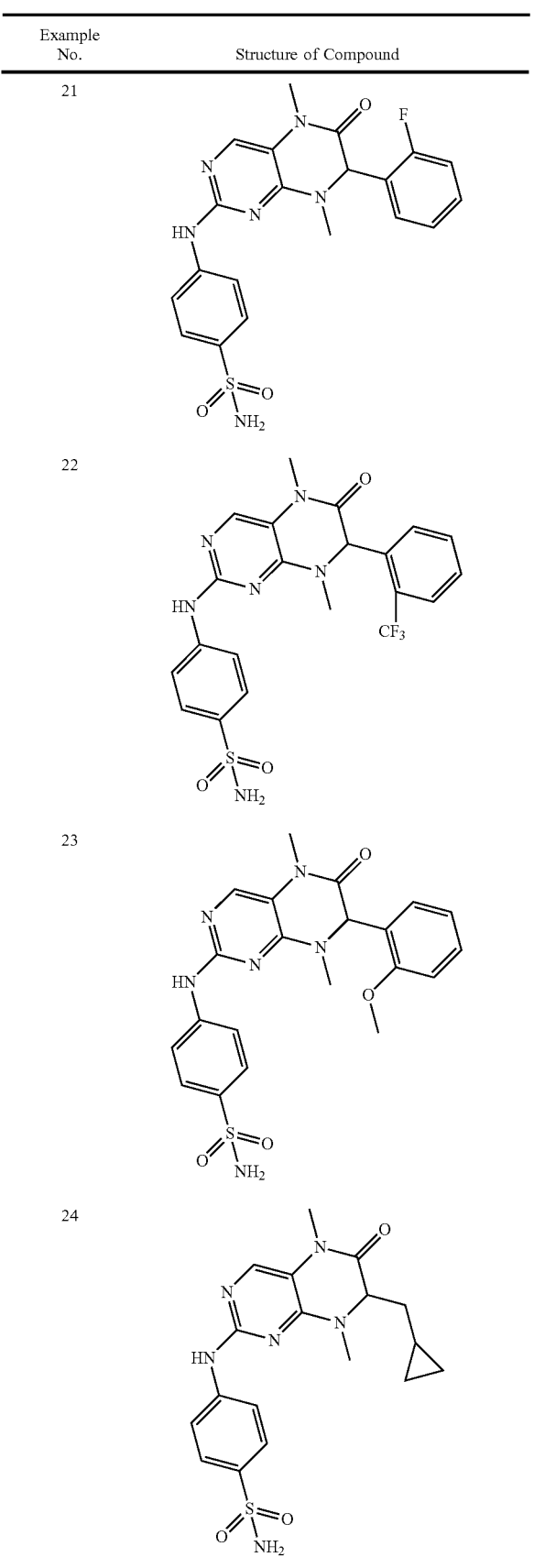
-continued
| Example No. | Structure of Compound |
|---|---|
| 25 | |
| 26 | |
| 27 | |
| 28 | |
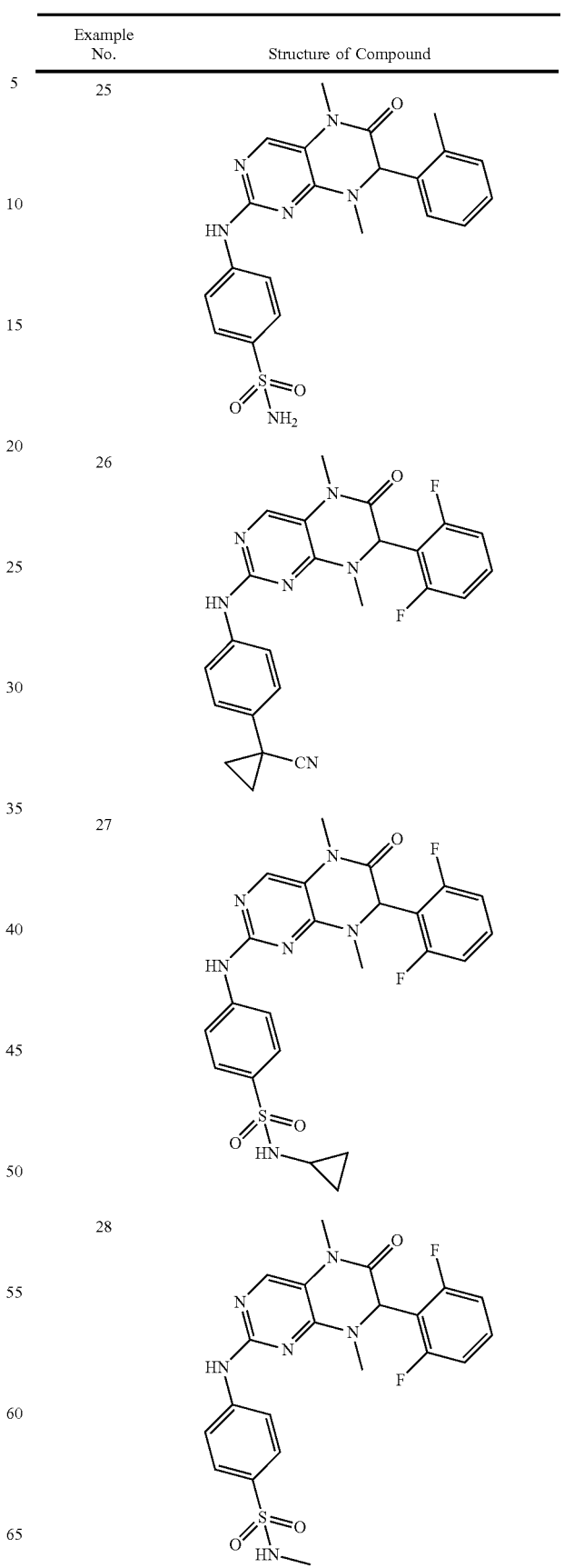

-continued
| Example No. | Structure of Compound |
|---|---|
| 29 | 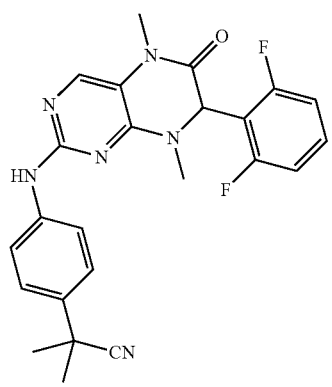 |
| 30 | 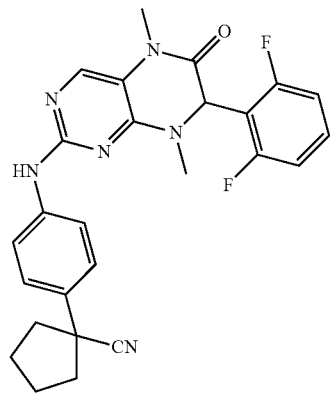 |
| 31 | 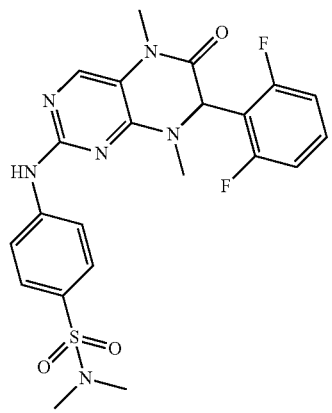 |
-continued
| Example No. | Structure of Compound |
|---|---|
| 32 | 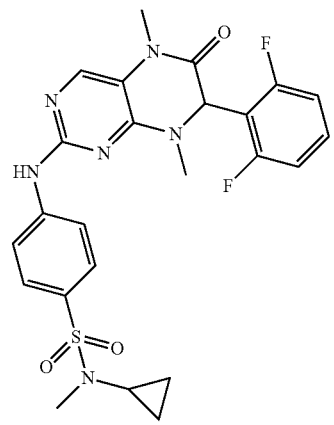 |
| 33 | 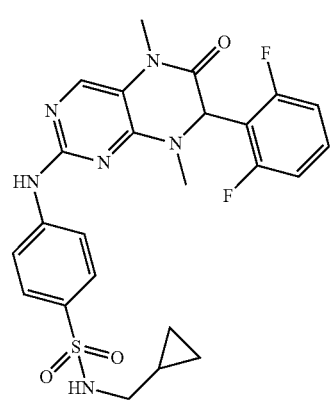 |
| 34 | 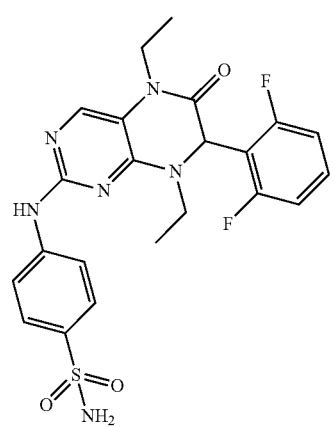 |

-continued
| Example No. | Structure of Compound |
|---|---|
| 35 | 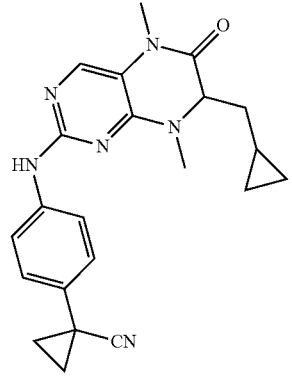 |
| 36 | 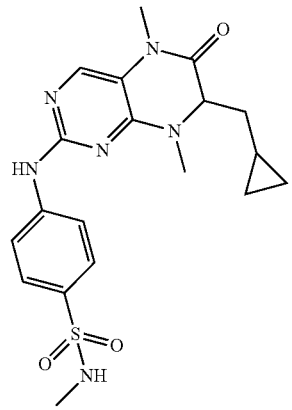 |
| 37 | 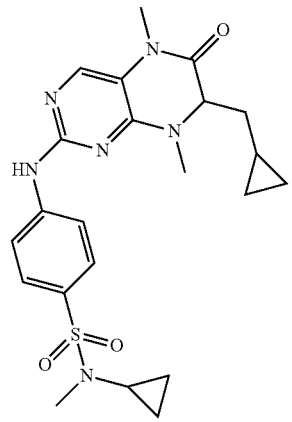 |
-continued
| Example No. | Structure of Compound |
|---|---|
| 38 | 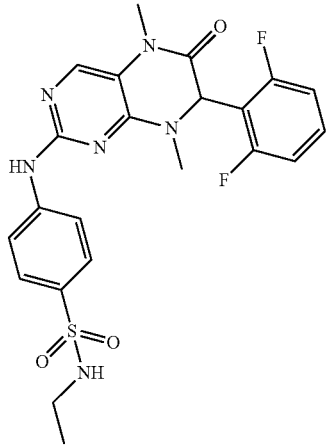 |
| 39 | 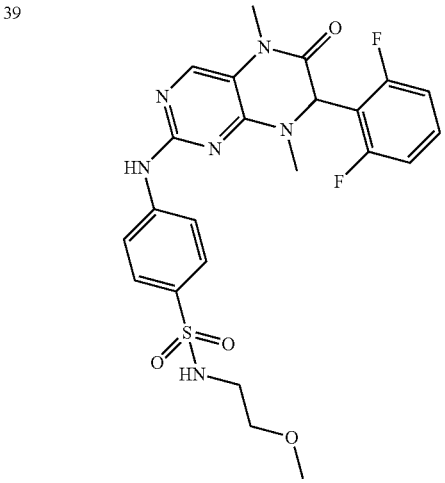 |
| 40 | 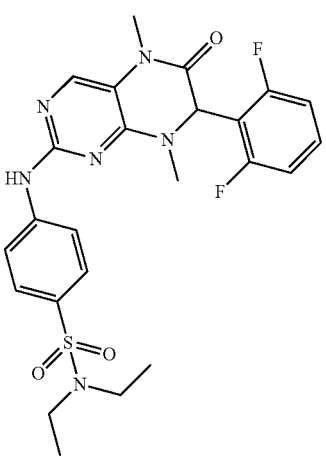 |

-continued
| Example No. | Structure of Compound |
|---|---|
| 41 | 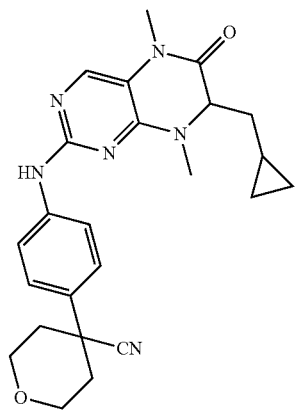 |
| 42 | 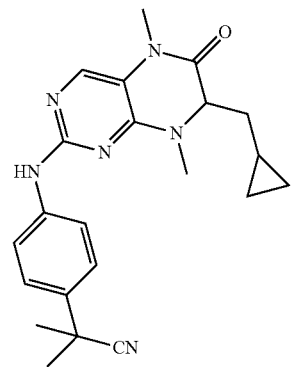 |
| 43 | 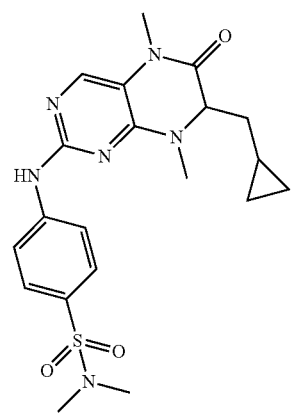 |
-continued
| Example No. | Structure of Compound |
|---|---|
| 44 | 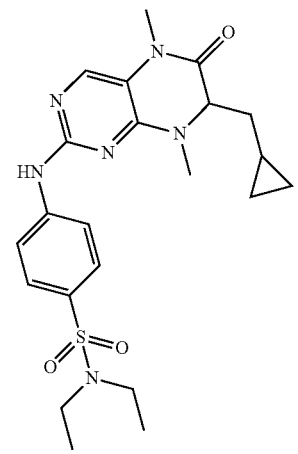 |
| 45 | 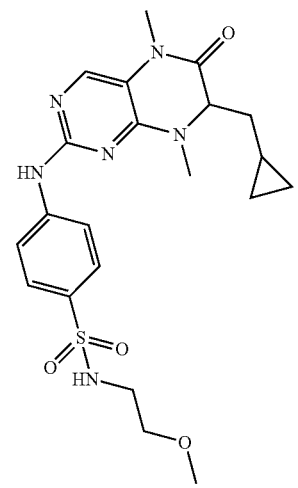 |
| 46 | 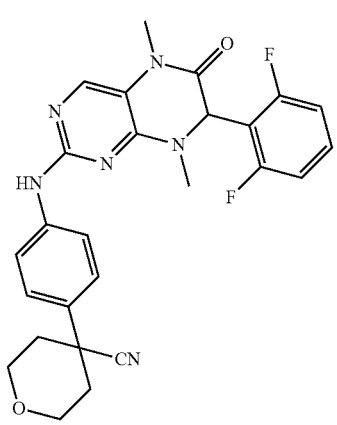 |

-continued

| Example No. | Structure of Compound |
|---|---|
| 47 | |
| 48 | |
| 49 | |
| 50 | |
| 51 | |
| 52 | |
| 53 | |

TABLE-continued
| Example No. | Structure of Compound |
|---|---|
| 54 | 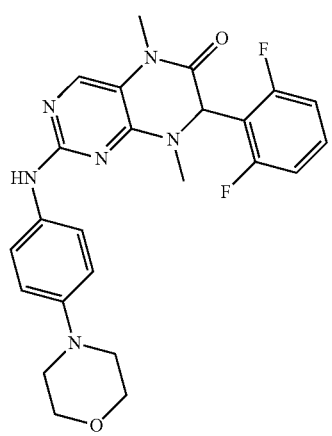 |
| 55 | 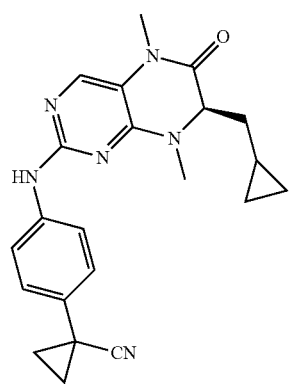 |
| 56 | 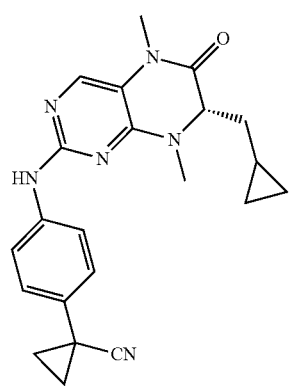 |
| 57 | 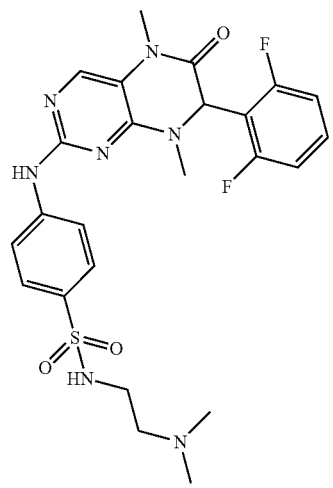 |
| 58 | 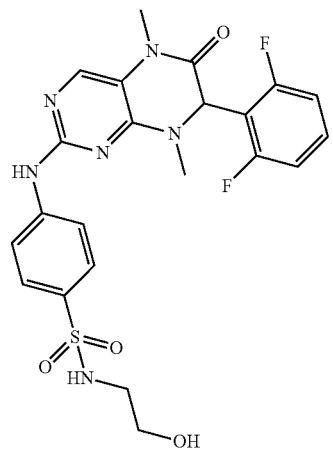 |
| 59 | 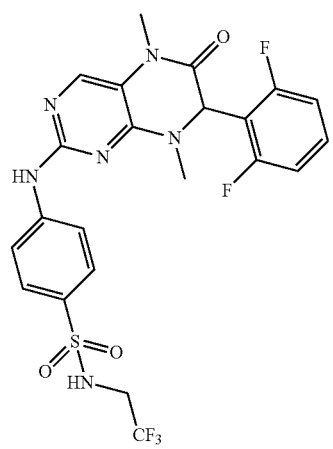 |

TABLE-continued
| Example No. | Structure of Compound |
|---|---|
| 60 | 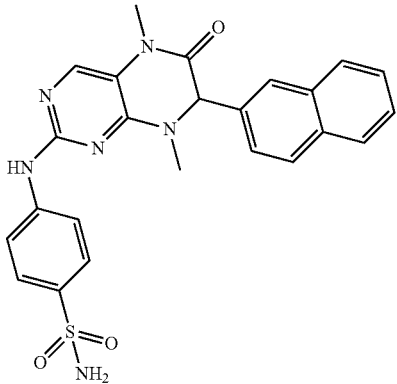 |
| 61 | 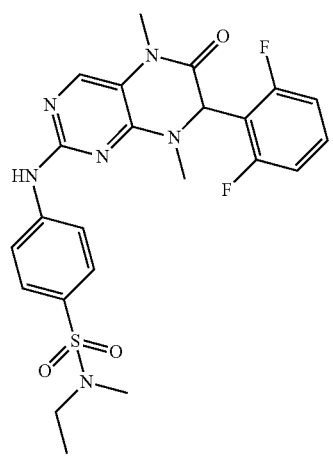 |
| 62 | 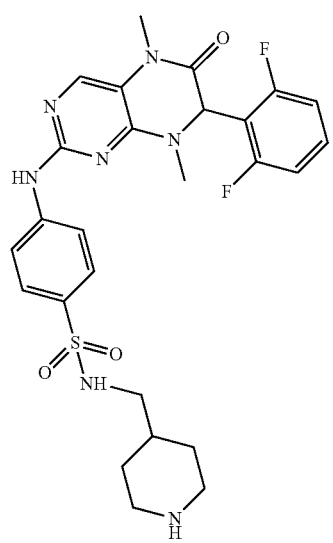 |
| 63 | 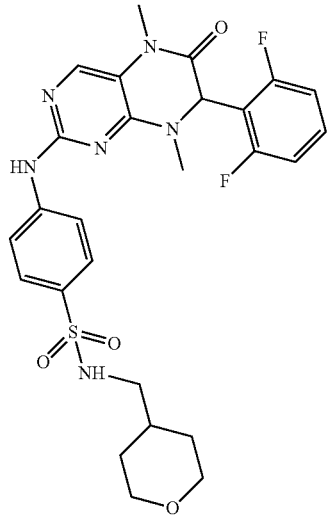 |
| 64 | 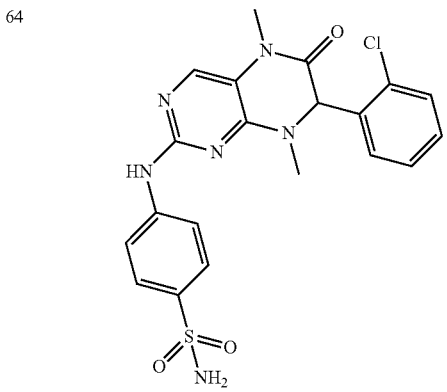 |
| 65 | 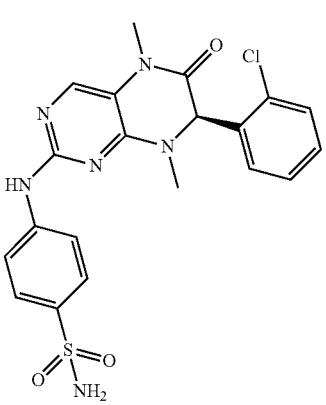 |

| Example No. | Structure of Compound |
|---|---|
| 66 | (structure) |
| 67 | (structure) |
| 68 | (structure) |
| 69 | (structure) |
| 70 | (structure) |

Example 1: 4-((7-(2,6-difluorophenyl)-5,8-dimethyl-6-oxo-5,6,7,8-tetrahydropteridin-2-yl)amino)benzsulfamide (reaction scheme showing A1 → A2 → A3 → A4 with reagents SOCl₂/MeOH 85°C overnight; 2,4-dichloro-5-nitropyrimidine, K₂CO₃, acetone, overnight; Fe, HOAc, 60°C, 2 h; CH₃I, NaH, −35°C, DMA, 2 h)

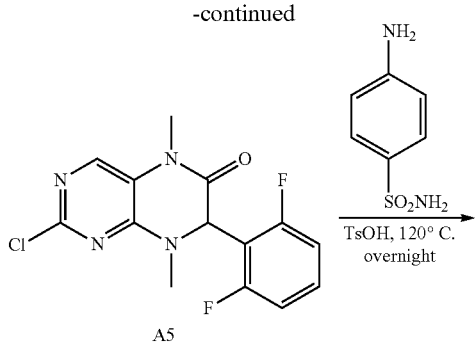

Methyl 2-amino-2-(2,6-difluorophenyl)acetate (A2): 3-2-amino-2-(2,6-difluorophenyl)acetic acid (2.0 g) and then methanol (30 ml) were added into a round bottom flask, followed by addition of thionyl chloride (1.2 ml) dropwise under an ice bath. The reaction system was reacted overnight at 85° C. After the completion of the reaction, the system was evaporated under reduced pressure to dry the solvent, and the obtained white solid was directly used in the next step.

Methyl 2-((2-chloro-5-nitropyrimidin-4-yl)amino)-2-(2,6-difluorophenyl)acetate (A3): methyl 2-amino-2-(2,6-difluorophenyl)acetate (2 g) and then acetone (30 ml) and potassium carbonate (2.2 g) were added into a round bottom flask, and then the system was cooled to −10° C. with an ice salt bath, and then a solution of 2,4-dichloro-5-nitropyrimidine (3.1 g) in acetone was slowly added. The reaction system was stirred overnight at room temperature. After the completion of the reaction, the reaction mixture was filtered, the solvent was removed from the filtrate under reduced pressure, and the residue was purified by pressurized silica gel column chromatography to obtain compound A3. LC/MS: M+H 359.0.

2-chloro-7-(2,6-difluorophenyl)-7,8-dihydropteridin-6 (5H)-one (A4): methyl 2-((2-chloro-5-nitropyrimidin-4-yl)amino)-2-(2,6-difluorophenyl)acetate (2.5 g) and then acetic acid (50 ml) and iron powder (3.9 g) were added into a round bottom flask. The reaction system was stirred at 60° C. for two hours. After the completion of the reaction, the reaction system was evaporated under reduced pressure to dry the solvent, and the resultant was neutralized to be alkaline with saturated sodium bicarbonate solution and was extracted with ethyl acetate. The organic phase was washed with water and saturated brine and dried with anhydrous sodium sulfate. The organic phase was filtered and evaporated to dryness under reduced pressure to obtain a crude product. The crude product was washed with diethyl ether to obtain compound A4. LC/MS: M+H 297.0.

2-chloro-7-(2,6-difluorophenyl)-5,8-dimethyl-7,8-dihydropteridin-6(5H)-one (A5): 2-chloro-7-(2,6-difluorophenyl)-7,8-dihydropteridin-6(5H)-one (2 g) and N,N-dimethylacetamide (10 ml) were added into a round bottom flask, and cooled to −35° C., followed by addition of iodomethane (0.9 ml) and then sodium hydride (615 mg), and the reaction system was stirred for two hours. After the completion of the reaction, the reaction mixture was quenched with water, and extracted with ethyl acetate. The organic phase was washed with water and saturated brine, respectively, and dried with anhydrous sodium sulfate. The organic phase was filtered and evaporated to dryness under reduced pressure to obtain a crude product. The crude product was washed with diethyl ether to obtain compound A5. LC/MS: M+H 325.0.

4-((7-(2,6-difluorophenyl)-5,8-dimethyl-6-oxo-5,6,7,8-tetrahydropteridin-2-yl)amino)benzsulfamide (1): 2-chloro-7-(2,6-difluorophenyl)-5,8-dimethyl-7,8-dihydropteridin-6 (5H)-one (100 mg), sulfanilamide (53 mg), p-toluenesulfonic acid (53 mg) and sec-butanol (5 ml) were added into a round bottom flask. The reaction system was stirred at 120° C. overnight. After the completion of the reaction, the reaction mixture was filtered, and washed with methanol and diethyl ether to obtain compound 1. LC/MS: M+H 461.1.

Example 2: 4-((5,8-dimethyl-6-oxo-7-phenyl-5,6,7,8-tetrahydropteridin-2-yl)amino)benzsulfamide

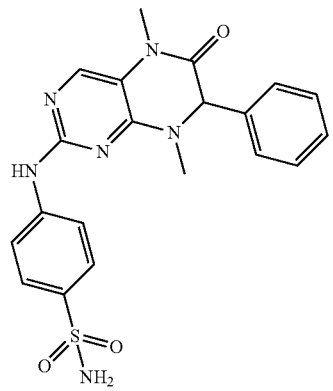 [SMILES: CN1C(=O)C(c2ccccc2)N(C)c2nc(Nc3ccc(S(N)(=O)=O)cc3)ncc21]

The synthesis of the compound of Example 2 is completed by using procedures similar as those in Example 1. MS(ESI) m/z (M+1)+: 425.14.

Example 3: 4-((7-benzyl-5,8-dimethyl-6-oxo-5,6,7,8-tetrahydropteridin-2-yl)amino)benzsulfamide

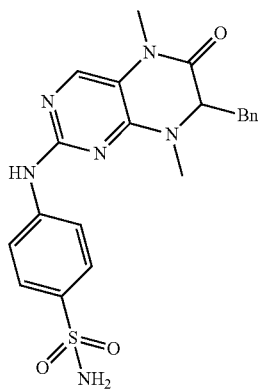 [SMILES: CN1C(=O)C(Cc2ccccc2)N(C)c2nc(Nc3ccc(S(N)(=O)=O)cc3)ncc21]

The synthesis of the compound of Example 3 is completed by using procedures similar as those in Example 1. MS(ESI) m/z (M+1)+: 439.15.

Example 4: (S)-4-((5,8-dimethyl-6-oxo-7-phenyl-5,6,7,8-tetrahydropteridin-2-yl)amino)benzsulfamide

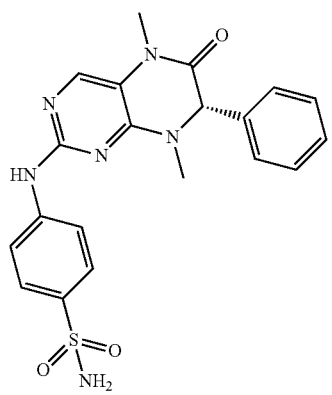 [SMILES: CN1C(=O)[C@H](c2ccccc2)N(C)c2nc(Nc3ccc(S(N)(=O)=O)cc3)ncc21]

The synthesis of the compound of Example 4 is completed by using procedures similar as those in Example 1. MS(ESI) m/z (M+1)+: 425.14.

Example 5: 4-((5,7,8-trimethyl-6-oxo-5,6,7,8-tetrahydropteridin-2-yl)amino)benzsulfamide

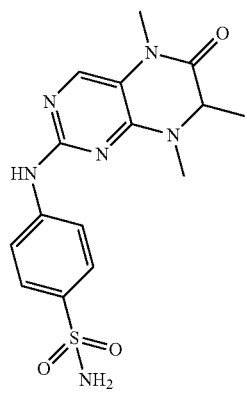 [SMILES: CC1C(=O)N(C)c2cnc(Nc3ccc(S(N)(=O)=O)cc3)nc2N1C]

The synthesis of the compound of Example 5 is completed by using procedures similar as those in Example 1. MS(ESI) m/z (M+1)+: 363.12.

Example 6: N-cyclopropyl-4-((5,8-dimethyl-6-oxo-7-phenyl-5,6,7,8-tetrahydropteridin-2-yl)amino)benzsulfamide

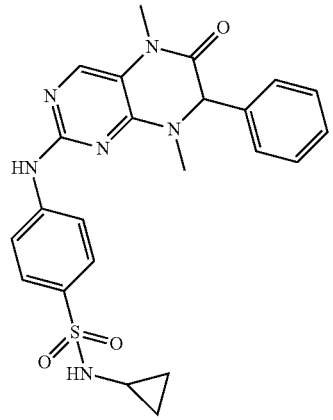 [SMILES: CN1C(=O)C(c2ccccc2)N(C)c2nc(Nc3ccc(S(=O)(=O)NC4CC4)cc3)ncc21]

The synthesis of the compound of Example 6 is completed by using procedures similar as those in Example 1. MS(ESI) m/z (M+1)+: 465.17.

Example 7: 4-((5',8'-dimethyl-6'-oxo-5',8'-dihydro-6'H-spiro[cyclopropan-1,7'-pteridin]-2'-yl)amino)benzsulfamide

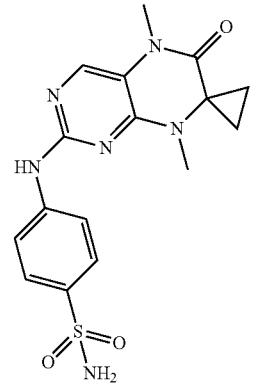 [SMILES: CN1C(=O)C2(CC2)N(C)c2nc(Nc3ccc(S(N)(=O)=O)cc3)ncc21]

The synthesis of the compound of Example 7 is completed by using procedures similar as those in Example 1. MS(ESI) m/z (M+1)+: 375.12.

Example 8: 4-((7-isopropyl-5,8-dimethyl-6-oxo-5,6,7,8-tetrahydropteridin-2-yl)amino)benzsulfamide

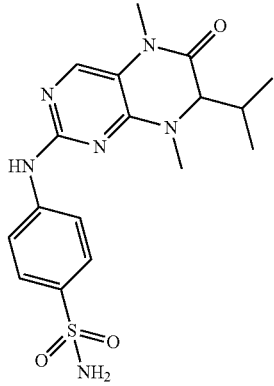 [SMILES: CC(C)C1C(=O)N(C)c2cnc(Nc3ccc(S(N)(=O)=O)cc3)nc2N1C]

The synthesis of the compound of Example 8 is completed by using procedures similar as those in Example 1. MS(ESI) m/z (M+1)+: 526.18.

Example 9: 4-((7-(4-fluorophenyl)-5,8-dimethyl-6-oxo-5,6,7,8-tetrahydropteridin-2-yl)amino)benzsulfamide

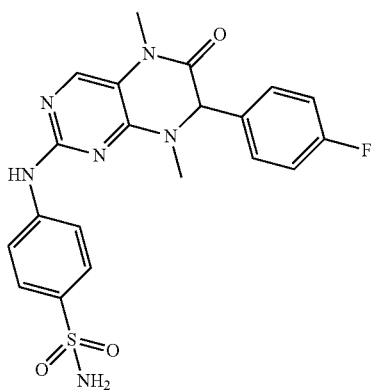 [SMILES: CN1C(=O)C(c2ccc(F)cc2)N(C)c2nc(Nc3ccc(S(N)(=O)=O)cc3)ncc21]

The synthesis of the compound of Example 9 is completed by using procedures similar as those in Example 1. MS(ESI) m/z (M+1)+: 443.13.

Example 10: (R)-4-((5,8-dimethyl-6-oxo-7-phenyl-5,6,7,8-tetrahydropteridin-2-yl)amino)benzsulfamide

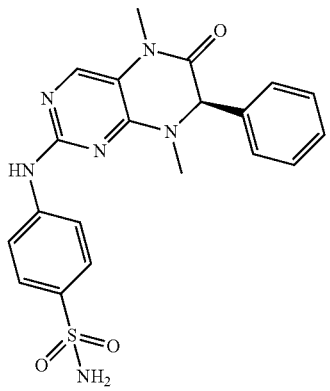 [SMILES: CN1C(=O)[C@@H](c2ccccc2)N(C)c2nc(Nc3ccc(S(N)(=O)=O)cc3)ncc21]

The synthesis of the compound of Example 10 is completed by using procedures similar as those in Example 1. MS(ESI) m/z (M+1)+: 425.14.

Example 11: 4-((7-(3-fluorophenyl)-5,8-dimethyl-6-oxo-5,6,7,8-tetrahydropteridin-2-yl)amino)benzsulfamide The synthesis of the compound of Example 11 is completed by using procedures similar as those in Example 1. MS(ESI) m/z (M+1)+: 443.13.

Example 12: 4-((7-(3-methoxyphenyl)-5,8-dimethyl-6-oxo-5,6,7,8-tetrahydropteridin-2-yl)amino)benzsulfamide

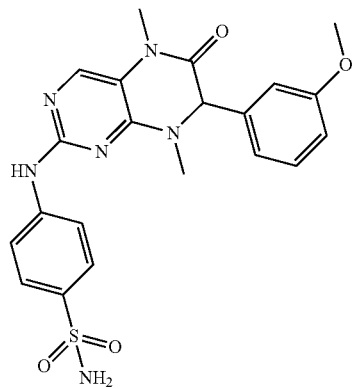 [SMILES: COc1cccc(C2C(=O)N(C)c3cnc(Nc4ccc(S(N)(=O)=O)cc4)nc3N2C)c1]

The synthesis of the compound of Example 12 is completed by using procedures similar as those in Example 1. MS(ESI) m/z (M+1)+: 455.15.

Example 13: 4-((7-(3-chlorophenyl)-5,8-dimethyl-6-oxo-5,6,7,8-tetrahydropteridin-2-yl)amino)benzsulfamide

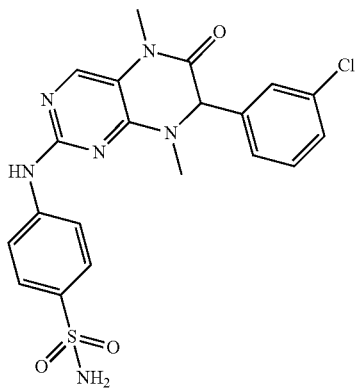 [SMILES: CN1C(=O)C(c2cccc(Cl)c2)N(C)c2nc(Nc3ccc(S(N)(=O)=O)cc3)ncc21]

The synthesis of the compound of Example 13 is completed by using procedures similar as those in Example 1. MS(ESI) m/z (M+1)+: 459.10.

Example 14: 4-((5',8'-dimethyl-6'-oxo-5',8'-dihydro-6'H-spiro[cyclopentan-1,7'-pteridin]-2'-yl)amino)benzsulfamide

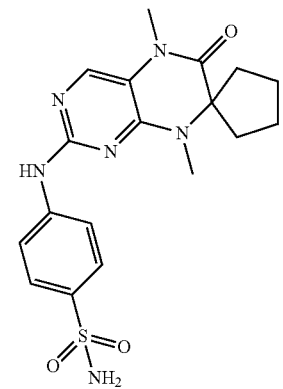

The synthesis of the compound of Example 14 is completed by using procedures similar as those in Example 1. MS(ESI) m/z (M+1)+: 403.15.

Example 15: 4-((5',8'-dimethyl-6'-oxo-5',8'-dihydro-6'H-spiro[cyclobutan-1,7'-pteridin]-2'-yl)amino)benzsulfamide

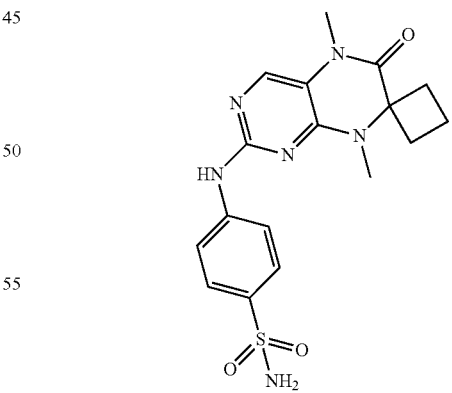

The synthesis of the compound of Example 15 is completed by using procedures similar as those in Example 1. MS(ESI) m/z (M+1)+: 389.14.

Example 16: 4-((7-isobutyl-5,8-dimethyl-6-oxo-5,6,7,8-tetrahydropteridin-2-yl)amino)benzsulfamide

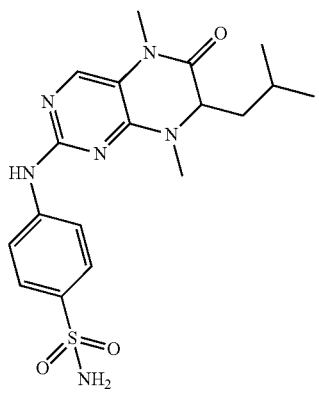 [SMILES: CC(C)CC1C(=O)N(C)c2cnc(Nc3ccc(S(N)(=O)=O)cc3)nc2N1C]

The synthesis of the compound of Example 16 is completed by using procedures similar as those in Example 1. MS(ESI) m/z (M+1)+: 405.17.

Example 17: 4-((5,8-dimethyl-6-oxo-7-propyl-5,6,7,8-tetrahydropteridin-2-yl)amino)benzsulfamide

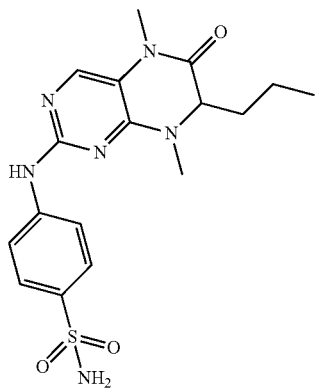 [SMILES: CCCC1C(=O)N(C)c2cnc(Nc3ccc(S(N)(=O)=O)cc3)nc2N1C]

The synthesis of the compound of Example 17 is completed by using procedures similar as those in Example 1. MS(ESI) m/z (M+1)+: 391.15.

Example 18: 4-((7-ethyl-5,8-dimethyl-6-oxo-5,6,7,8-tetrahydropteridin-2-yl)amino)benzsulfamide

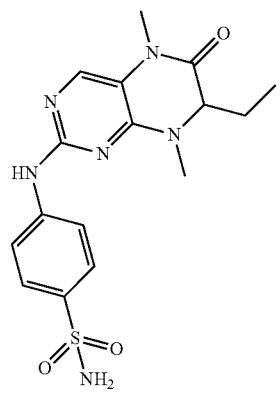 [SMILES: CCC1C(=O)N(C)c2cnc(Nc3ccc(S(N)(=O)=O)cc3)nc2N1C]

The synthesis of the compound of Example 18 is completed by using procedures similar as those in Example 1. MS(ESI) m/z (M+1)+: 377.14.

Example 19: 4-((7-cyclopropyl-5,8-dimethyl-6-oxo-5,6,7,8-tetrahydropteridin-2-yl)amino)benzsulfamide

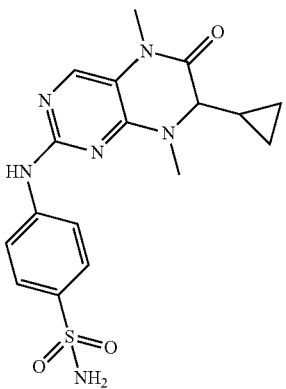 [SMILES: CN1C(=O)C(C2CC2)N(C)c2nc(Nc3ccc(S(N)(=O)=O)cc3)ncc21]

The synthesis of the compound of Example 19 is completed by using procedures similar as those in Example 1. MS(ESI) m/z (M+1)+: 389.14.

Example 20: 4-((5,8-dimethyl-6-oxo-7-(thien-2-yl)-5,6,7,8-tetrahydropteridin-2-yl)amino)benzsulfamide

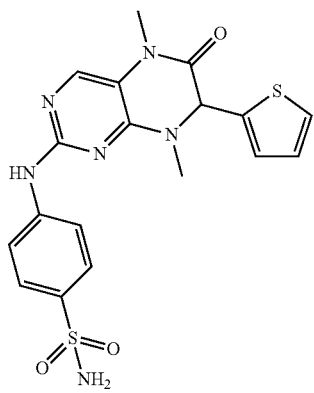

The synthesis of the compound of Example 20 is completed by using procedures similar as those in Example 1. MS(ESI) m/z (M+1)+: 431.09.

Example 21: 4-((7-(2-fluorophenyl)-5,8-dimethyl-6-oxo-5,6,7,8-tetrahydropteridin-2-yl)amino)benzsulfamide

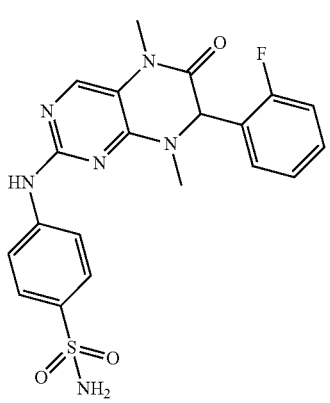

The synthesis of the compound of Example 21 is completed by using procedures similar as those in Example 1. MS(ESI) m/z (M+1)+: 443.13.

Example 22: 4-((5,8-dimethyl-6-oxo-7-(2-(trifluoromethyl)phenyl)-5,6,7,8-tetrahydropteridin-2-yl)amino)benzsulfamide

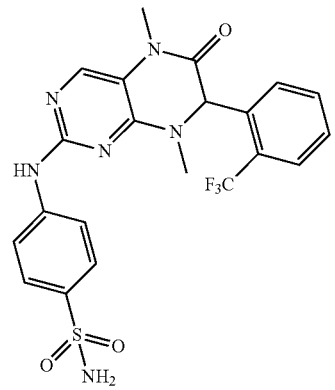

The synthesis of the compound of Example 22 is completed by using procedures similar as those in Example 1. MS(ESI) m/z (M+1)+: 493.12.

Example 23: 4-((7-(2-methoxyphenyl)-5,8-dimethyl-6-oxo-5,6,7,8-tetrahydropteridin-2-yl)amino)benzsulfamide

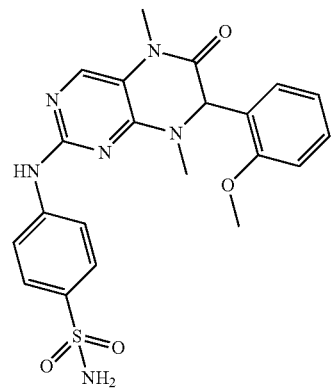 [SMILES: COc1ccccc1C1C(=O)N(C)c2cnc(Nc3ccc(S(N)(=O)=O)cc3)nc2N1C]

The synthesis of the compound of Example 23 is completed by using procedures similar as those in Example 1. MS(ESI) m/z (M+1)+: 455.15.

Example 24: 4-((7-(cyclopropylmethyl)-5,8-dimethyl-6-oxo-5,6,7,8-tetrahydropteridin-2-yl)amino)benzsulfamide

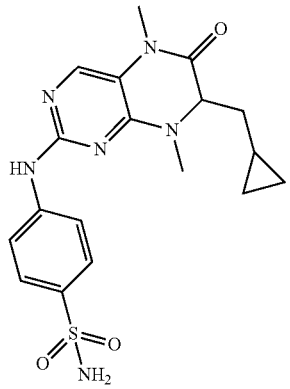 [SMILES: CN1C(=O)C(CC2CC2)N(C)c2nc(Nc3ccc(S(N)(=O)=O)cc3)ncc21]

The synthesis of the compound of Example 24 is completed by using procedures similar as those in Example 1. MS(ESI) m/z (M+1)+: 403.15.

Example 25: 4-((5,8-dimethyl-6-oxo-7-(o-methylphenyl)-5,6,7,8-tetrahydropteridin-2-yl)amino)benzsulfamide

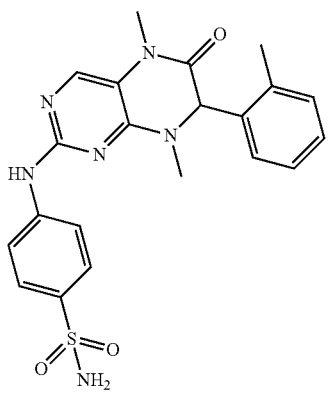

The synthesis of the compound of Example 25 is completed by using procedures similar as those in Example 1. MS(ESI) m/z (M+1)+: 439.15.

Example 26: 1-(4-((7-(2,6-difluorophenyl)-5,8-dimethyl-6-oxo-5,6,7,8-tetrahydropteridin-2-yl)amino)phenyl)cyclopropan-1-formonitrile

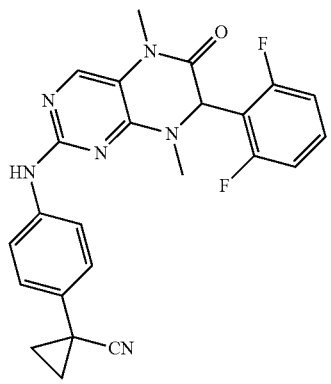 [SMILES: CN1C(=O)C(c2c(F)cccc2F)N(C)c2nc(Nc3ccc(C4(C#N)CC4)cc3)ncc21]

The synthesis of the compound of Example 26 is completed by using procedures similar as those in Example 1. MS(ESI) m/z (M+1)+: 477.17.

Example 27: N-cyclopropyl-4-((7-(2,6-difluorophenyl)-5,8-dimethyl-6-oxo-5,6,7,8-tetrahydropteridin-2-yl)amino)benzsulfamide

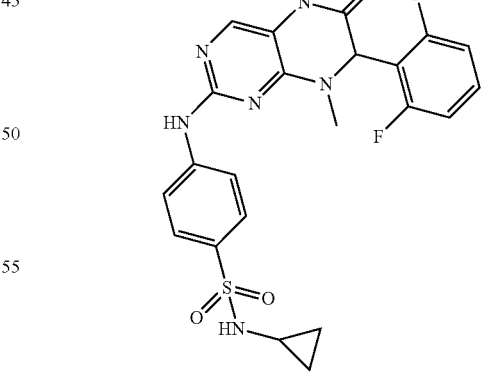

The synthesis of the compound of Example 27 is completed by using procedures similar as those in Example 1. MS(ESI) m/z (M+1)+: 501.15.

Example 28: 4-((7-(2,6-difluorophenyl)-5,8-dimethyl-6-oxo-5,6,7,8-tetrahydropteridin-2-yl)amino)-N-methylbenzsulfamide

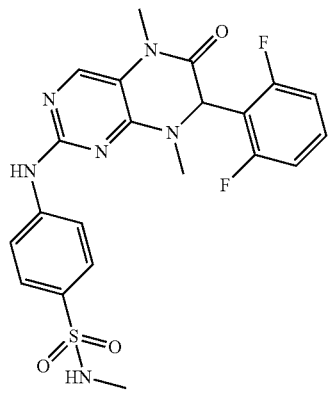 [SMILES: CNS(=O)(=O)c1ccc(Nc2ncc3c(n2)N(C)C(c2c(F)cccc2F)C(=O)N3C)cc1]

The synthesis of the compound of Example 28 is completed by using procedures similar as those in Example 1. MS(ESI) m/z (M+1)+: 475.13.

Example 29: 2-(4-((7-(2,6-difluorophenyl)-5,8-dimethyl-6-oxo-5,6,7,8-tetrahydropteridin-2-yl)amino)phenyl)-2-methylpropionitrile

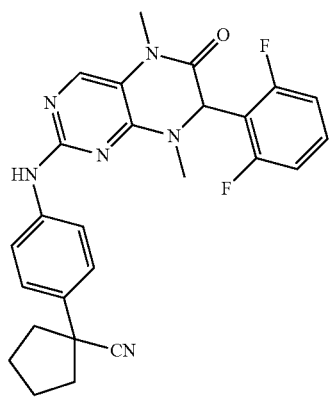 [SMILES: CN1C(=O)C(c2c(F)cccc2F)N(C)c2nc(Nc3ccc(C4(C#N)CCCC4)cc3)ncc21]

The synthesis of the compound of Example 29 is completed by using procedures similar as those in Example 1. MS(ESI) m/z (M+1)+: 449.19.

Example 30: 1-(4-((7-(2,6-difluorophenyl)-5,8-dimethyl-6-oxo-5,6,7,8-tetrahydropteridin-2-yl)amino)phenyl)cyclopentan-1-nitrile

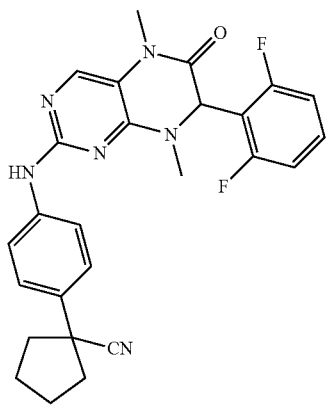

The synthesis of the compound of Example 30 is completed by using procedures similar as those in Example 1. MS(ESI) m/z (M+1)+: 475.20.

Example 31: 4-((7-(2,6-difluorophenyl)-5,8-dimethyl-6-oxo-5,6,7,8-tetrahydropteridin-2-yl)amino)-N,N-dimethylbenzsulfamide

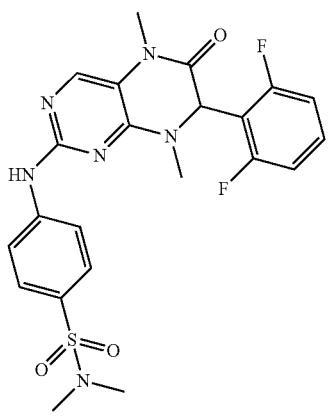 [SMILES: CN1C(=O)C(c2c(F)cccc2F)N(C)c2nc(Nc3ccc(S(=O)(=O)N(C)C)cc3)ncc21]

The synthesis of the compound of Example 31 is completed by using procedures similar as those in Example 1. MS(ESI) m/z (M+1)+: 489.15.

Example 32: N-cyclopropyl-4-((7-(2,6-difluorophenyl)-5,8-dimethyl-6-oxo-5,6,7,8-tetrahydropteridin-2-yl)amino)-N-methylbenzsulfamide

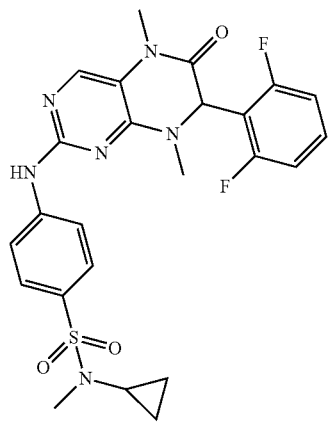 [SMILES: CN1C(=O)C(c2c(F)cccc2F)N(C)c2nc(Nc3ccc(S(=O)(=O)N(C)C4CC4)cc3)ncc21]

The synthesis of the compound of Example 32 is completed by using procedures similar as those in Example 1. MS(ESI) m/z (M+1)+: 515.16.

Example 33: N-(cyclopropylmethyl)-4-((7-(2,6-difluorophenyl)-5,8-dimethyl-6-oxo-5,6,7,8-tetrahydropteridin-2-yl)amino)benzsulfamide

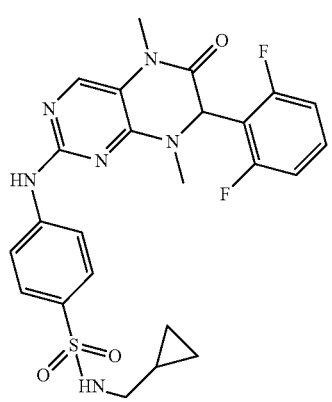 [SMILES: CN1C(=O)C(c2c(F)cccc2F)N(C)c2nc(Nc3ccc(S(=O)(=O)NCC4CC4)cc3)ncc21]

The synthesis of the compound of Example 33 is completed by using procedures similar as those in Example 1. MS(ESI) m/z (M+1)+: 515.16.

Example 34: 4-((7-(2,6-difluorophenyl)-5,8-diethyl-6-oxo-5,6,7,8-tetrahydropteridin-2-yl)amino)benzsulfamide

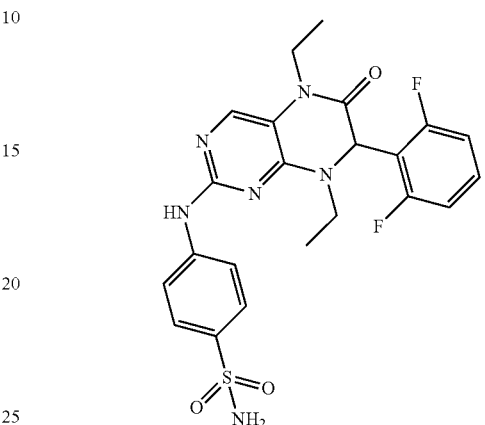

The synthesis of the compound of Example 34 is completed by using procedures similar as those in Example 1. MS(ESI) m/z (M+1)+: 489.15.

Example 35: 1-(4-((7-(cyclopropylmethyl)-5,8-dimethyl-6-oxo-5,6,7,8-tetrahydropteridin-2-yl)amino)phenyl)cyclopropan-1-formonitrile

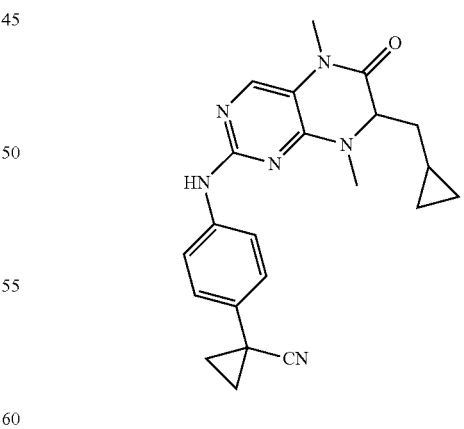

The synthesis of the compound of Example 35 is completed by using procedures similar as those in Example 1. MS(ESI) m/z (M+1)+: 389.21.

Example 36: 4-((7-(cyclopropylmethyl)-5,8-dimethyl-6-oxo-5,6,7,8-tetrahydropteridin-2-yl)amino)-N-methylbenzsulfamide

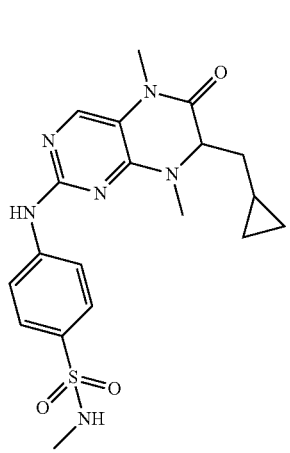 [SMILES: CNS(=O)(=O)c1ccc(Nc2ncc3c(n2)N(C)C(CC2CC2)C(=O)N3C)cc1]

The synthesis of the compound of Example 36 is completed by using procedures similar as those in Example 1. MS(ESI) m/z (M+1)+: 417.17.

Example 37: N-cyclopropyl-4-((7-(cyclopropylmethyl)-5,8-dimethyl-6-oxo-5,6,7,8-tetrahydropteridin-2-yl)amino)-N-methylbenzsulfamide

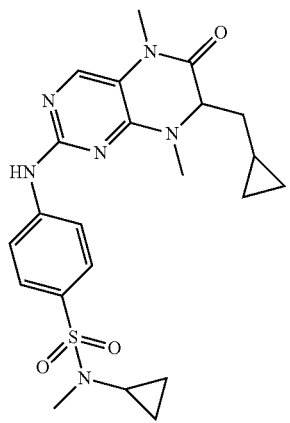 [SMILES: CN1C(=O)C(CC2CC2)N(C)c2nc(Nc3ccc(S(=O)(=O)N(C)C4CC4)cc3)ncc21]

The synthesis of the compound of Example 37 is completed by using procedures similar as those in Example 1. MS(ESI) m/z (M+1)+: 457.20.

Example 38: 4-((7-(2,6-difluorophenyl)-5,8-dimethyl-6-oxo-5,6,7,8-tetrahydropteridin-2-yl)amino)-N-ethylbenzsulfamide

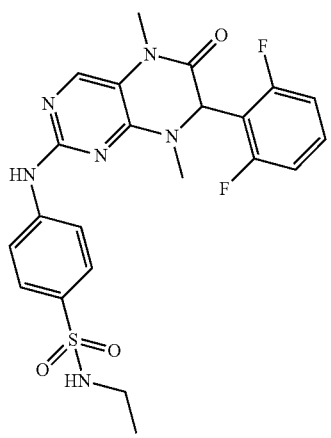

The synthesis of the compound of Example 38 is completed by using procedures similar as those in Example 1. MS(ESI) m/z (M+1)+: 489.15.

Example 39: 4-((7-(2,6-difluorophenyl)-5,8-dimethyl-6-oxo-5,6,7,8-tetrahydropteridin-2-yl)amino)-N-(2-methoxyethyl)benzsulfamide

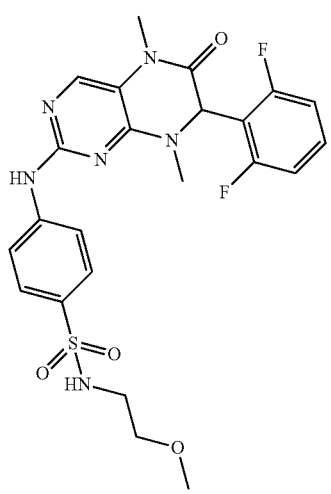 [SMILES: COCCNS(=O)(=O)c1ccc(Nc2ncc3c(n2)N(C)C(c2c(F)cccc2F)C(=O)N3C)cc1]

The synthesis of the compound of Example 39 is completed by using procedures similar as those in Example 1. MS(ESI) m/z (M+1)+: 519.16.

Example 40: 4-((7-(2,6-difluorophenyl)-5,8-dimethyl-6-oxo-5,6,7,8-tetrahydropteridin-2-yl)amino)-N,N-diethylbenzsulfamide

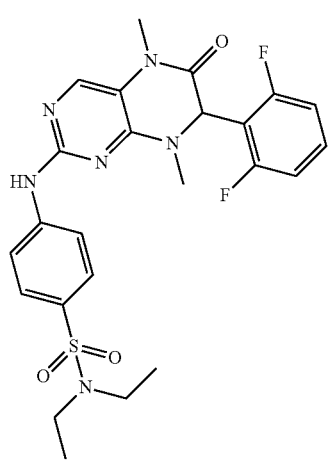 [SMILES: CCN(CC)S(=O)(=O)c1ccc(Nc2ncc3c(n2)N(C)C(c2c(F)cccc2F)C(=O)N3C)cc1]

The synthesis of the compound of Example 40 is completed by using procedures similar as those in Example 1. MS(ESI) m/z (M+1)+: 517.18.

Example 41: 4-(4-((7-(cyclopropylmethyl)-5,8-dimethyl-6-oxo-5,6,7,8-tetrahydropteridin-2-yl)amino)phenyl)tetrahydro-2H-pyran-4-formonitrile

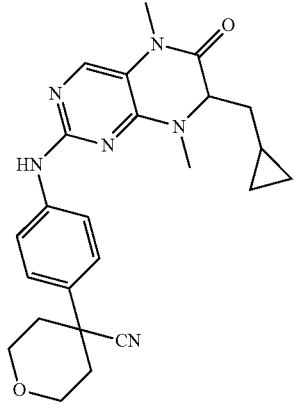 [SMILES: CN1C(=O)C(CC2CC2)N(C)c2nc(Nc3ccc(C4(C#N)CCOCC4)cc3)ncc21]

The synthesis of the compound of Example 41 is completed by using procedures similar as those in Example 1. MS(ESI) m/z (M+1)+: 433.23.

Example 42: 2-(4-((7-(cyclopropylmethyl)-5,8-dimethyl-6-oxo-5,6,7,8-tetrahydropteridin-2-yl)amino)phenyl)-2-methylpropionitrile

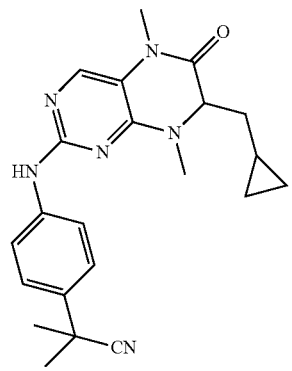 [SMILES: CN1C(=O)C(CC2CC2)N(C)c2nc(Nc3ccc(C(C)(C)C#N)cc3)ncc21]

The synthesis of the compound of Example 42 is completed by using procedures similar as those in Example 1. MS(ESI) m/z (M+1)+: 391.22.

Example 43: 4-((7-(cyclopropylmethyl)-5,8-dimethyl-6-oxo-5,6,7,8-tetrahydropteridin-2-yl)amino)-N,N-dimethylbenzsulfamide

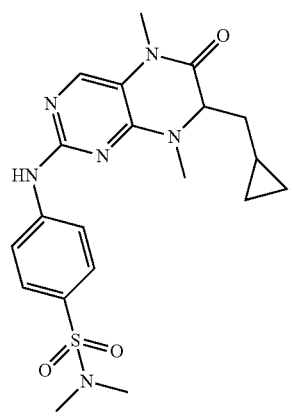 [SMILES: CN1C(=O)C(CC2CC2)N(C)c2nc(Nc3ccc(S(=O)(=O)N(C)C)cc3)ncc21]

The synthesis of the compound of Example 43 is completed by using procedures similar as those in Example 1. MS(ESI) m/z (M+1)+: 431.18.

Example 44: 4-((7-(cyclopropylmethyl)-5,8-dimethyl-6-oxo-5,6,7,8-tetrahydropteridin-2-yl)amino)-N,N-diethylbenzsulfamide

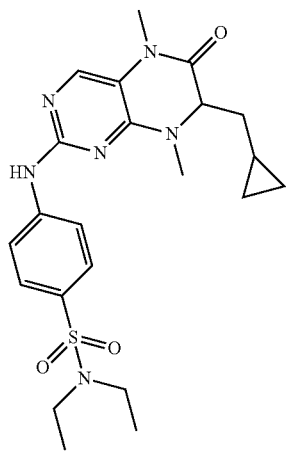 [SMILES: CCN(CC)S(=O)(=O)c1ccc(Nc2ncc3c(n2)N(C)C(CC2CC2)C(=O)N3C)cc1]

The synthesis of the compound of Example 44 is completed by using procedures similar as those in Example 1. MS(ESI) m/z (M+1)+: 459.21.

Example 45: 4-((7-(cyclopropylmethyl)-5,8-dimethyl-6-oxo-5,6,7,8-tetrahydropteridin-2-yl)amino)-N-(2-methoxyethyl)benzsulfamide

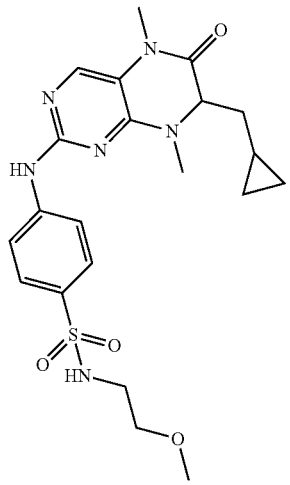 [SMILES: COCCNS(=O)(=O)c1ccc(Nc2ncc3c(n2)N(C)C(CC2CC2)C(=O)N3C)cc1]

The synthesis of the compound of Example 45 is completed by using procedures similar as those in Example 1. MS(ESI) m/z (M+1)+: 461.19.

Example 46: 4-(4-((7-(2,6-difluorophenyl)-5,8-dimethyl-6-oxo-5,6,7,8-tetrahydropteridin-2-yl)amino)phenyl)tetrahydro-2H-pyran-4-nitrile

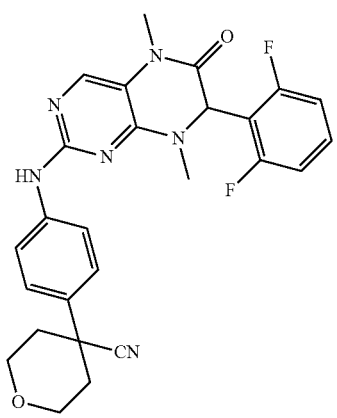 [SMILES: CN1C(=O)C(c2c(F)cccc2F)N(C)c2nc(Nc3ccc(C4(C#N)CCOCC4)cc3)ncc21]

The synthesis of the compound of Example 46 is completed by using procedures similar as those in Example 1. MS(ESI) m/z (M+1)+: 491.20.

Example 47: (R)-4-((7-(2,6-difluorophenyl)-5,8-dimethyl-6-oxo-5,6,7,8-tetrahydropteridin-2-yl)amino)benzsulfamide

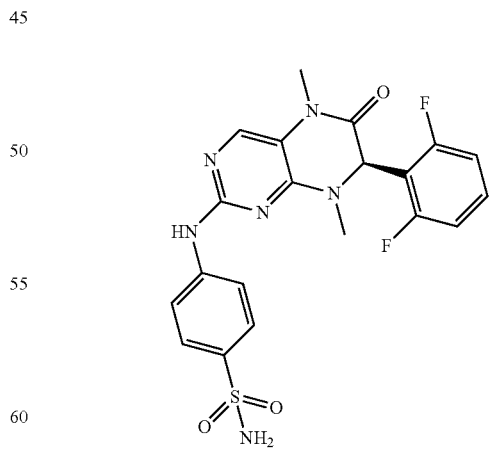

The synthesis of the compound of Example 47 is completed by using procedures similar as those in Example 1. MS(ESI) m/z (M+1)+: 461.12.

Example 48: (S)-4-((7-(2,6-difluorophenyl)-5,8-dimethyl-6-oxo-5,6,7,8-tetrahydropteridin-2-yl)amino)benzsulfamide

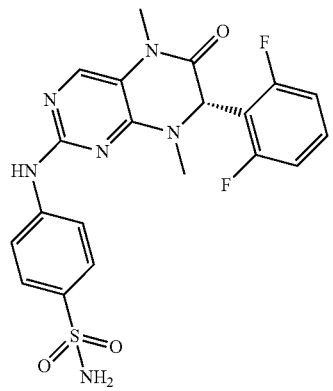 [SMILES: CN1C(=O)[C@H](c2c(F)cccc2F)N(C)c2nc(Nc3ccc(S(N)(=O)=O)cc3)ncc21]

The synthesis of the compound of Example 48 is completed by using procedures similar as those in Example 1. MS(ESI) m/z (M+1)+: 461.12.

Example 49: (R)-4-((7-(cyclopropylmethyl)-5,8-dimethyl-6-oxo-5,6,7,8-tetrahydropteridin-2-yl)amino)benzsulfamide

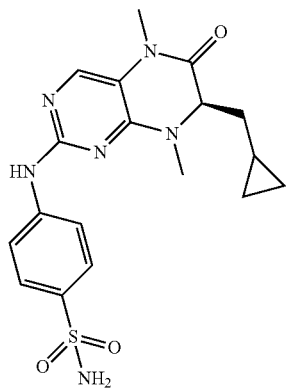 [SMILES: CN1C(=O)[C@@H](CC2CC2)N(C)c2nc(Nc3ccc(S(N)(=O)=O)cc3)ncc21]

The synthesis of the compound of Example 49 is completed by using procedures similar as those in Example 1. MS(ESI) m/z (M+1)+: 403.15.

Example 50: (S)-4-((7-(cyclopropylmethyl)-5,8-dimethyl-6-oxo-5,6,7,8-tetrahydropteridin-2-yl)amino)benzsulfamide

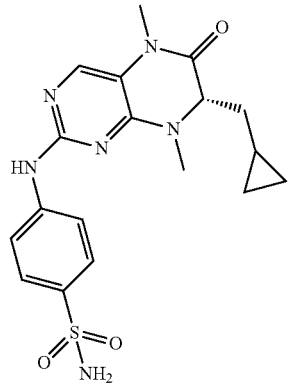 [SMILES: CN1C(=O)[C@H](CC2CC2)N(C)c2nc(Nc3ccc(S(N)(=O)=O)cc3)ncc21]

The synthesis of the compound of Example 50 is completed by using procedures similar as those in Example 1. MS(ESI) m/z (M+1)+: 403.15.

Example 51: 4-((7-(cyclopropylmethyl)-5,8-diisopropyl-6-oxo-5,6,7,8-tetrahydropteridin-2-yl)amino)benzsulfamide

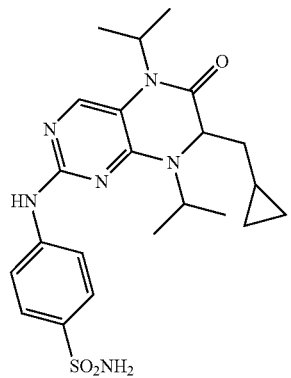 [SMILES: CC(C)N1C(=O)C(CC2CC2)N(C(C)C)c2nc(Nc3ccc(S(N)(=O)=O)cc3)ncc21]

The synthesis of the compound of Example 51 is completed by using procedures similar as those in Example 1. MS(ESI) m/z (M+1)+: 459.21.

Example 52: 4-((7-(cyclopropylmethyl)-5,8-diethyl-6-oxo-5,6,7,8-tetrahydropteridin-2-yl)amino)benzsulfamide

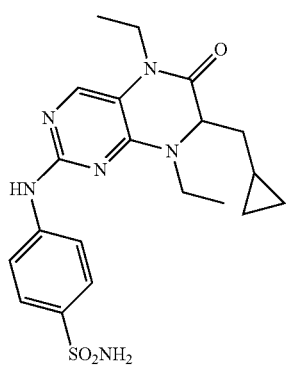 [SMILES: CCN1C(=O)C(CC2CC2)N(CC)c2nc(Nc3ccc(S(N)(=O)=O)cc3)ncc21]

The synthesis of the compound of Example 52 is completed by using procedures similar as those in Example 1. MS(ESI) m/z (M+1)+: 431.18.

Example 53: 7-(2,6-difluorophenyl)-5,8-dimethyl-2-((4-(4-methylpiperazin-1-yl)phenyl)amino)-7,8-dihydropteridin-6(5H)-one

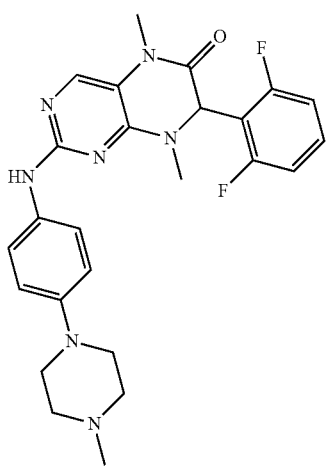 [SMILES: CN1CCN(c2ccc(Nc3ncc4c(n3)N(C)C(c3c(F)cccc3F)C(=O)N4C)cc2)CC1]

The synthesis of the compound of Example 53 is completed by using procedures similar as those in Example 1. MS(ESI) m/z (M+1)+: 480.23.

Example 54: 7-(2,6-difluorophenyl)-5,8-dimethyl-2-((4-morpholinophenyl)amino)-7,8-dihydropteridin-6(5H)-one

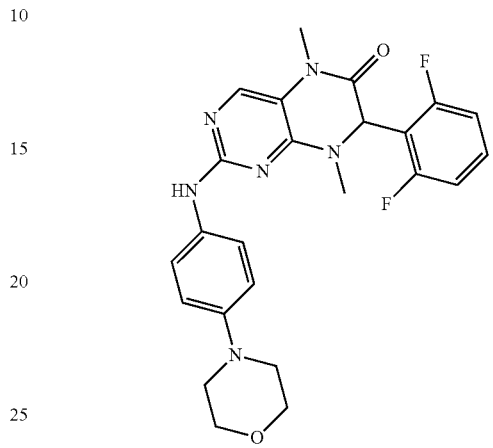

The synthesis of the compound of Example 54 is completed by using procedures similar as those in Example 1. MS(ESI) m/z (M+1)+: 467.20.

Example 55: (R)-1-(4-((7-(cyclopropylmethyl)-5,8-dimethyl-6-oxo-5,6,7,8-tetrahydropteridin-2-yl)amino)phenyl)cyclopropan-1-formonitrile

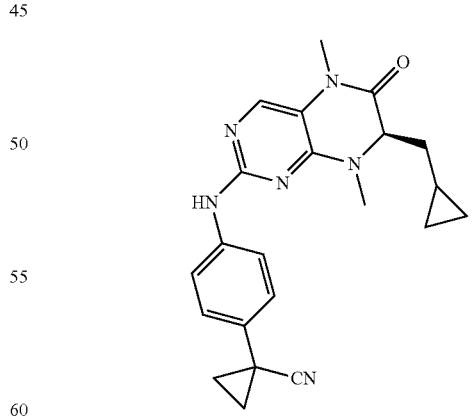

The synthesis of the compound of Example 55 is completed by using procedures similar as those in Example 1. MS(ESI) m/z (M+1)+: 389.20.

Example 56: (S)-1-(4-((7-(cyclopropylmethyl)-5,8-dimethyl-6-oxo-5,6,7,8-tetrahydropteridin-2-yl)amino)phenyl)cyclopropan-1-formonitrile

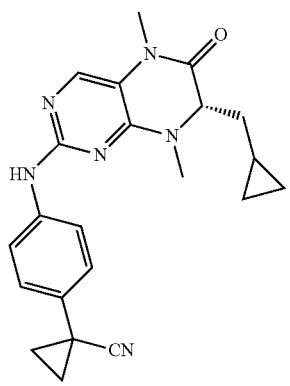

The synthesis of the compound of Example 56 is completed by using procedures similar as those in Example 1. MS(ESI) m/z (M+1)+: 389.20.

Example 57: (4-((7-(2,6-difluorophenyl)-5,8-dimethyl-6-oxo-5,6,7,8-tetrahydropteridin-2-yl)amino)-N-(2-(dimethylamino)ethyl)benzsulfamide

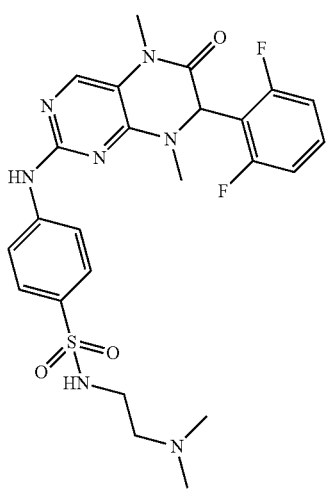 [SMILES: CN(C)CCNS(=O)(=O)c1ccc(Nc2ncc3c(n2)N(C)C(c2c(F)cccc2F)C(=O)N3C)cc1]

The synthesis of the compound of Example 57 is completed by using procedures similar as those in Example 1. MS(ESI) m/z (M+1)+: 532.19.

Example 58: 4-((7-(2,6-difluorophenyl)-5,8-dimethyl-6-oxo-5,6,7,8-tetrahydropteridin-2-yl)amino)-N-(2-hydroxyethyl)benzsulfamide

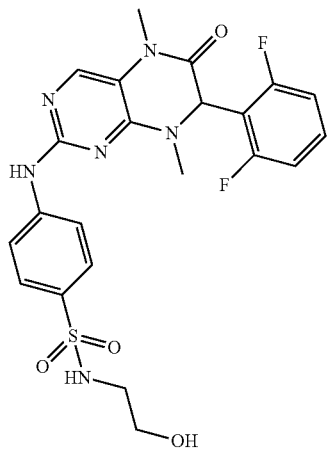 [SMILES: CN1C(=O)C(c2c(F)cccc2F)N(C)c2nc(Nc3ccc(S(=O)(=O)NCCO)cc3)ncc21]

The synthesis of the compound of Example 58 is completed by using procedures similar as those in Example 1. MS(ESI) m/z (M+1)+: 505.14.

Example 59: 4-((7-(2,6-difluorophenyl)-5,8-dimethyl-6-oxo-5,6,7,8-tetrahydropteridin-2-yl)amino)-N-(2,2,2-trifluoroethyl)benzsulfamide

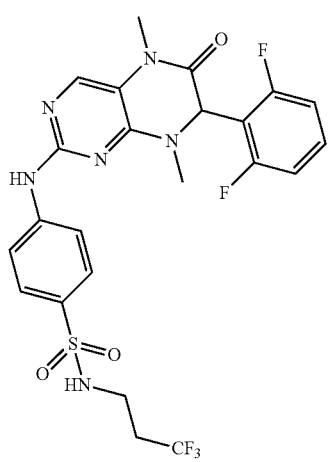

The synthesis of the compound of Example 59 is completed by using procedures similar as those in Example 1. MS(ESI) m/z (M+1)+: 543.12.

Example 60: 4-((5,8-dimethyl-7-(naphth-2-yl)-6-oxo-5,6,7,8-tetrahydropteridin-2-yl)amino)benzsulfamide

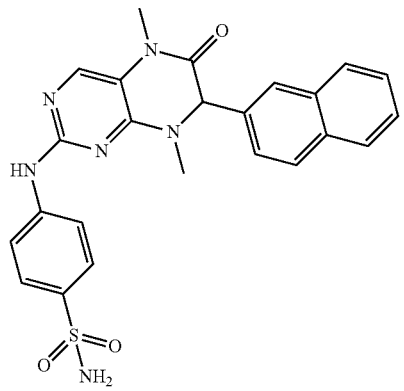 [SMILES: CN1C(=O)C(c2ccc3ccccc3c2)N(C)c2nc(Nc3ccc(S(N)(=O)=O)cc3)ncc21]

The synthesis of the compound of Example 60 is completed by using procedures similar as those in Example 1. MS(ESI) m/z (M+1)+: 475.16.

Example 61: 4-((7-(2,6-difluorophenyl)-5,8-dimethyl-6-oxo-5,6,7,8-tetrahydropteridin-2-yl)amino)-N-ethyl-N-methylbenzsulfamide

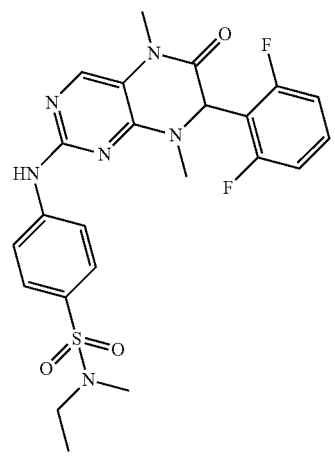 [SMILES: CCN(C)S(=O)(=O)c1ccc(Nc2ncc3c(n2)N(C)C(c2c(F)cccc2F)C(=O)N3C)cc1]

The synthesis of the compound of Example 61 is completed by using procedures similar as those in Example 1. MS(ESI) m/z (M+1)+: 503.17.

Example 62: 4-((7-(2,6-difluorophenyl)-5,8-dimethyl-6-oxo-5,6,7,8-tetrahydropteridin-2-yl)amino)-N-(piperidin-4-ylmethyl)benzsulfamide

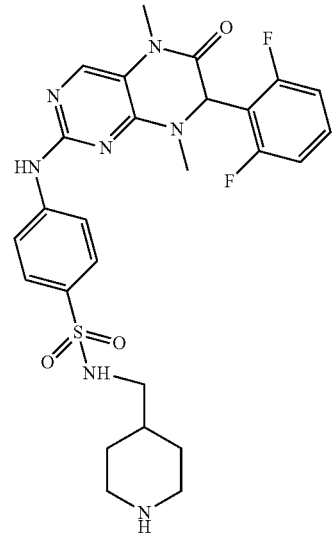

The synthesis of the compound of Example 62 is completed by using procedures similar as those in Example 1. MS(ESI) m/z (M+1)+: 558.21.

Example 63: 4-((7-(2,6-difluorophenyl)-5,8-dimethyl-6-oxo-5,6,7,8-tetrahydropteridin-2-yl)amino)-N-((tetrahydro-2H-pyran-4-yl)methyl) benzsulfamide

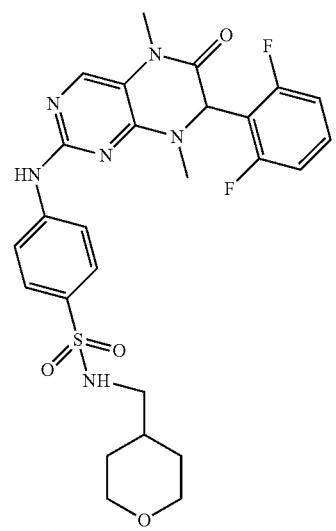

The synthesis of the compound of Example 63 is completed by using procedures similar as those in Example 1. MS(ESI) m/z (M+1)+: 559.19.

Example 64: 47-(2-chlorophenyl)-5,8-dimethyl-6-oxo-5,6,7,8-tetrahydropteridin-2-yl)amino)benzsulfamide

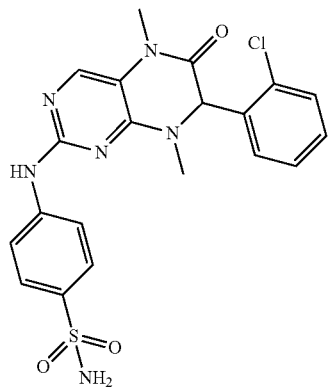

The synthesis of the compound of Example 64 is completed by using procedures similar as those in Example 1. MS(ESI) m/z (M+1)+: 459.10.

Example 65: (R)-4-((7-(2-chlorophenyl)-5,8-dimethyl-6-oxo-5,6,7,8-tetrahydropteridin-2-yl)amino)benzsulfamide

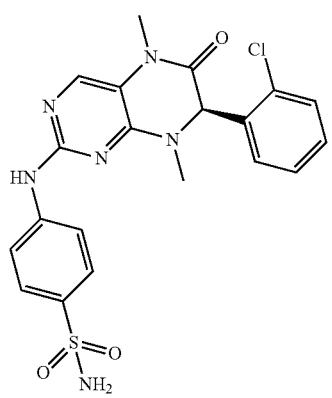 [SMILES: CN1C(=O)[C@@H](c2ccccc2Cl)N(C)c2nc(Nc3ccc(S(N)(=O)=O)cc3)ncc21]

The synthesis of the compound of Example 65 is completed by using procedures similar as those in Example 1. MS(ESI) m/z (M+1)+: 459.10.

Example 66: (S)-4-((7-(2-chlorophenyl)-5,8-dimethyl-6-oxo-5,6,7,8-tetrahydropteridin-2-yl)amino)benzsulfamide

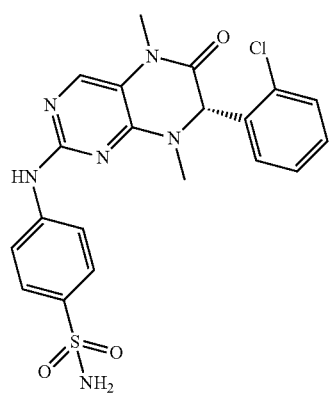 [SMILES: CN1C(=O)[C@H](c2ccccc2Cl)N(C)c2nc(Nc3ccc(S(N)(=O)=O)cc3)ncc21]

The synthesis of the compound of Example 66 is completed by using procedures similar as those in Example 1. MS(ESI) m/z (M+1)+: 459.10.

Example 67: 4-((5',8'-dimethyl-6'-oxo-5',8'-dihydro-6'H-spiro[cyclohexyl-1,7'-pteridin]-2'-yl)amino)benzsulfamide

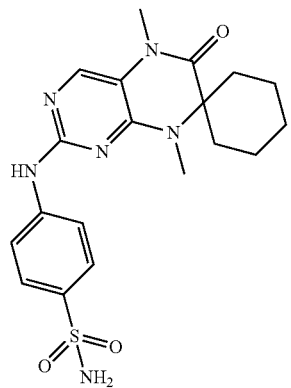 [SMILES: CN1C(=O)C2(CCCCC2)N(C)c2nc(Nc3ccc(S(N)(=O)=O)cc3)ncc21]

The synthesis of the compound of Example 67 is completed by using procedures similar as those in Example 1. MS(ESI) m/z (M+1)+: 417.17.

Example 68: 4-((7-cyclohexyl-5,8-dimethyl-6-oxo-5,6,7,8-tetrahydropteridin-2-yl)amino)benzsulfamide

Example 70: (S)-4-((5,8-dimethyl-6-oxo-7-(o-methylphenyl)-5,6,7,8-tetrahydropteridin-2-yl)amino)benzsulfamide

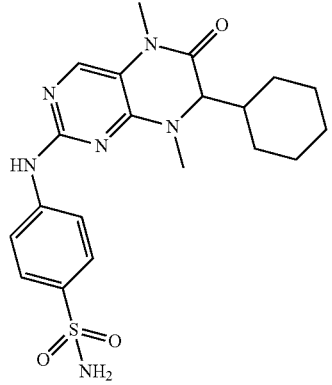 [SMILES: CN1C(=O)C(C2CCCCC2)N(C)c2nc(Nc3ccc(S(N)(=O)=O)cc3)ncc21]

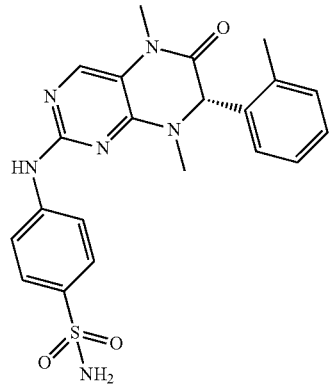 [SMILES: Cc1ccccc1[C@H]1C(=O)N(C)c2cnc(Nc3ccc(S(N)(=O)=O)cc3)nc2N1C]

The synthesis of the compound of Example 70 is completed by using procedures similar as those in Example 1. MS(ESI) m/z (M+1)+: 439.16.

Example 71: In Vitro Enzyme Activity Test

The synthesis of the compound of Example 68 is completed by using procedures similar as those in Example 1. MS(ESI) m/z (M+1)+: 431.19.

The $IC_{50}$ values of the compounds against MST1 were determined. The protein kinase MST1 and the substrate were obtained from commercial sources.

5.4 μL of protein kinase MST1 diluted to a certain concentration (final concentration was 2.5 ng/μL) and 1 μL of serially diluted drug compounds and control compound XMU-MP-1 were taken to react at room temperature for 10 minutes (final drug concentrations were 10 μM, 1 μM, 0.3 μM, 0.1 μM, 0.03 μM, 0.01 μM, 0.003 μM, 0.001 μM, respectively).

Example 69: (R)-4-((5,8-dimethyl-6-oxo-7-(o-methylphenyl)-5,6,7,8-tetrahydropteridin-2-yl)amino)benzsulfamide 6 μL of a mixture of ATP (with a final reaction concentration of 50 μM) and substrate was added to the above reaction tube to react at 37° C. for 1 hour. The reaction buffer was 40 mM Tris, 7.5; 20 mM $MgCl_2$; 0.1 mg/ml BSA; 50 μM DTT.

5 μL of the kinase mixture after the reaction was taken to a 384-well plate, and 5 μL of ADP-GLO™ reagent was added thereto. After reaction at room temperature for 40 minutes, the kinase reaction was terminated and the remaining ATP was consumed.

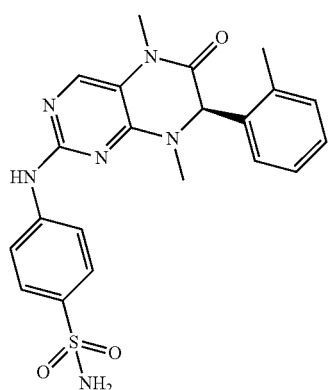

10 μL of a kinase detection reagent was added to convert ADP into ATP, and a coupled luciferase/luciferin reaction was utilized to detect the newly synthesized ATP. Envision was used to read and plot the data, and calculate the $IC_{50}$ value. The results were listed in Table 1 below.

The data showed that the activity of our compounds against MST1 reached or were superior over that of the control compound XMU-MP-1.

TABLE 1

| Compound No. | MST1 ($IC_{50}$/μM) |
|---|---|
| XMU-MP-1 | 121 |
| Compound 1 | 23 |
| Compound 4 | 197.3 |
| Compound 6 | 142.7 |
| Compound 7 | 102.6 |
| Compound 10 | 98.7 |
| Compound 11 | 133.9 |

The synthesis of the compound of Example 69 is completed by using procedures similar as those in Example 1. MS(ESI) m/z (M+1)+: 439.16.

TABLE 1-continued

| Compound No. | MST1 (IC$_{50}$/μM) |
|---|---|
| Compound 14 | 128.9 |
| Compound 15 | 140.9 |
| Compound 16 | 76.7 |
| Compound 17 | 206.3 |
| Compound 19 | 136.7 |
| Compound 20 | 87.9 |
| Compound 21 | 75.3 |
| Compound 22 | 56.3 |
| Compound 25 | 22.7 |
| Compound 27 | 112.6 |
| Compound 32 | 31.6 |
| Compound 33 | 79.6 |
| Compound 38 | 51.6 |

Example 72: Liver Injury Repair Experiment

C57BL/6 mice, male, 20 g, were maintained in a SPF animal room. Thirty C57BL/6 mice were fasted for 12 hours overnight, and 5 mice of which were intraperitoneally injected with normal saline to act as a normal control group, and the other 25 mice were intraperitoneally injected with paracetamol (APAP) (purchased from Sigma)-600 mg/kg, and randomly divided into 5 groups after 30 minutes, wherein the 5 groups include vehicle (5% DMSO in water), compound 1-1-po, compound 1-2-po, compound 1-4-po, XMU-MP-1-ip groups. Mice in the vehicle group were administered intragastrically with vehicle control; mice in the compound 1-1-po, compound 1-2-po, compound 1-4-po groups were administered intragastrically with compound 1 at 1 mg/kg, 2 mg/kg or 4 mg/kg, respectively; mice in the XMU-MP-1-ip group were intraperitoneally administered with the control compound XMU-MP-1 at 1 mg/kg. After the administration, the body weight of the mice was monitored and the survival status of the mice was observed.

The experimental results showed that the weight of the mice decreased significantly after the administration of paracetamol. The mice in the vehicle control group all died within 48 hours. The groups of intragastrical administration of compound 1 and the group of intraperitoneal administration of the control compound XMU-MP-1 all reduced death of mice after APAP administration. The survival rate of the mice in the compound 1-1-po group reached 80%, and the mice in the compound 1-2-po, compound 1-4-po and XMU-MP-1-ip groups all escaped from death. Meanwhile, the weight of mice administered with compound 1 and XMU-MP-1 can gradually recover, suggesting that in this common drug-induced liver injury model, compound 1, a MST small molecule inhibitor, can achieve an effect on inhibiting liver injury by oral administration similar as that by intraperitoneal administration of the control compound XMU-MP-1.

Example 73: Effect on Signaling Pathways of Pancreatic β Cells

Figure 2:
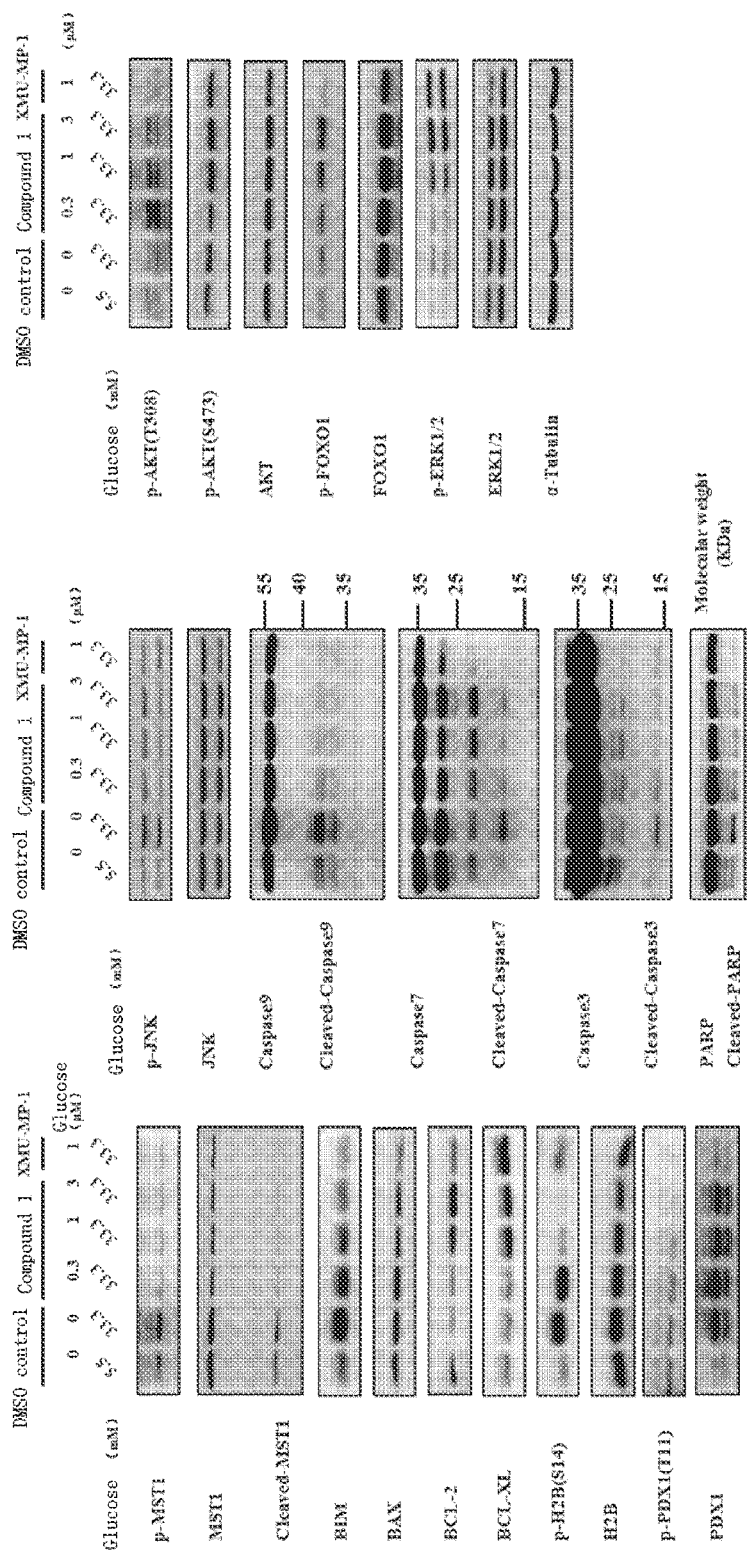
FIG. 2 shows the effect of Compound 1 and the control compound XMU-MP-1 on the signaling pathway of pancreatic β-cells.

The effects of compound 1 and the control compound XMU-MP-1 on MST1 signaling pathway such as autophosphorylation of MST1, apoptosis signaling pathway such as cleavage of four proteins Caspase9/7/3 and PARP, expression of BIM, BAX, BCL-2, BCL-XL protein, proliferation-related signaling pathway such as autophosphorylation of AKT and ERK, and phosphorylation and protein expression of insulin secretion transcription factor PDX1 were tested in mouse pancreatic β-cells, MIN-6 cells (Hunan Fenghuishengwu technology Co., Ltd.). Compound 1 of different concentrations (0 μM, 0.3 μM, 1 μM, 3 μM in DMSO) and XMU-MP-1 of 1 μM (in DMSO) were used to treat the cell line for 72 hours in a medium with a glucose content of 33.3 mM, respectively. One of the control DMSO group involved 5.5 mM glucose and the other one involved 33.3 mM glucose. The samples were collected. The effects of compound 1 and the control compound XMU-MP-1 on the signaling pathways of pancreatic β-cells were shown in FIG. 2.

The test results showed that the administration of the compound at 1 μM can significantly inhibit the autophosphorylation of MST1, down-regulate the expression of pro-apoptosis-related proteins such as BIM to a certain extent and promote the expression of the anti-apoptotic protein BCL-XL to a certain extent, and inhibit the cleavage of the four proteins Caspase9/7/3 and PARP to a certain extent. This indicated that compound 1 can inhibit the apoptosis of pancreatic β-cells. Compound 1 has a certain inhibitory effect on the phosphorylation of the transcription factor PDX1 related to insulin secretion and promotes the expression of PDX1 to a certain extent, indicating that compound 1 can promote the insulin secretion of cells. As to growth-related signaling pathways, compound 1 does not affect AKT autophosphorylation, but can activate ERK autophosphorylation, indicating that compound 1 can promote cell proliferation to a certain extent, while the control group has much death debris of cells, which is harmful to cells to a certain extent.

Figure 3:
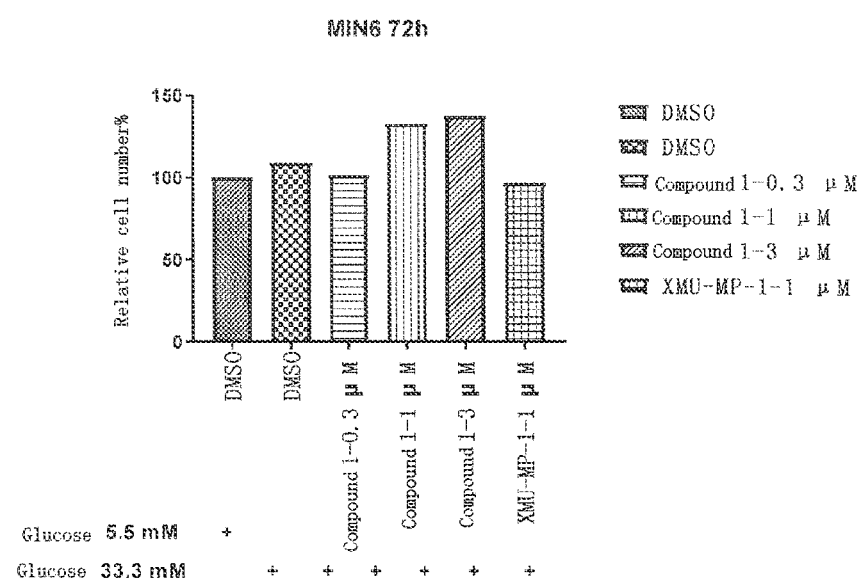
FIG. 3 shows the effect of Compound 1 and the control compound XMU-MP-1 on the proliferation of pancreatic β-cells.

JIMBIO cell counter (EXCEL HERO TECHNOLOGY LIMITED) was used to detect the effect on the proliferation of MIN-6 cells after 72 hours of the administration. As shown in FIG. 3, the control compound XMU-MP-1 was toxic to MIN6 cells to a certain extent when administered at 1 μM, and the number of cells was found to be reduced to a certain extent, while the compound 1 of the invention can promote cell proliferation after administration, as the drug concentration increases.

INDUSTRIAL APPLICABILITY

The invention provides a MST1 kinase inhibitor, which comprises a compound of Formula (I) or a pharmaceutically acceptable salt, solvate, ester, acid, metabolite or prodrug thereof. The invention also provides use and a method for the prevention or treatment of diseases related to MST1 kinase activity by the compound of Formula (I), especially use and a method for the prevention or treatment of hepatitis and liver damage, and diabetes. Therefore, the above inhibitor can be prepared into corresponding medicaments, which are suitable for industrial applications.

Although the invention has been described herein in detail, the invention is not limited hereto. Those skilled in the art can modify the invention based on the principles of the invention, and thus various modifications made in accordance with the principles of the invention should be understood as falling within the protection scope of the invention.

What is claimed is:

1. A kinase inhibitor compound of Formula (I) or a pharmaceutically acceptable salt, solvate, ester, acid, or prodrug thereof, Formula (I)

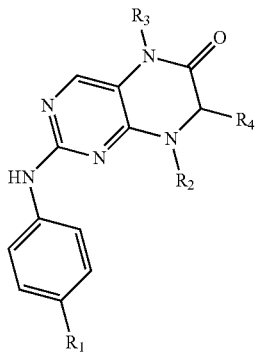

wherein,
R₁ is selected from

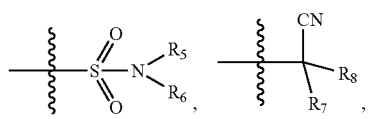

and C3-C6 heterocycloalkyl;

R₂ and R₃ are each independently selected from C1-C6 alkyl;

R₄ is selected from C3-C6 cycloalkyl, C4-C8 cycloalkylalkyl, C2-C6 spirocycloalkyl, aryl optionally substituted with 1-3 R₉, aryl-C1-C6 alkyl optionally substituted with 1-3 R₉ and heteroaryl optionally substituted with 1-3 R₉;

R₅ and R₆ are each independently selected from hydrogen, C1-C6 alkyl, C3-C6 cycloalkyl, C4-C8 cycloalkylalkyl, C3-C6 heterocycloalkyl, hydroxyl C1-C6 alkyl, C1-C6 alkylamino, C1-C6 haloalkyl, C1-C6 alkylamino C1-C6 alkyl, C1-C6 alkoxy C1-C6 alkyl, and C3-C6 heterocyclyl C1-C6 alkyl;

R₇ and R₈ are each independently selected from C1-C6 alkyl, or R₇ and R₈, together with the carbon atom attached thereto, form C3-C6 cycloalkyl or C3-C6 heterocyclyl; and R₉ is selected from halogen, C1-C6 alkyl, C1-C6 alkoxy, and C1-C6 haloalkyl.

2. The kinase inhibitor compound according to claim 1, wherein
R₁ is selected from

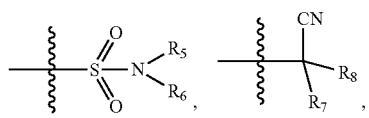

piperazinyl optionally substituted with C1-C6 alkyl, and morpholinyl optionally substituted with C1-C6 alkyl;

R₂ and R₃ are each independently selected from C1-C3 alkyl;

R₄ is selected from C3-C6 cycloalkyl, C4-C8 cycloalkylalkyl, C2-C6 spirocycloalkyl, phenyl optionally substituted with 1-3 R₉, naphthyl optionally substituted with 1-3 R₉, phenylmethyl optionally substituted with 1-3 R₉, and thienyl optionally substituted with 1-3 R₉;

R₅ and R₆ are each independently selected from hydrogen, C1-C6 alkyl, C3-C6 cycloalkyl, C4-C8 cycloalkylalkyl, C3-C6 heterocycloalkyl, hydroxyl C1-C6 alkyl, C1-C6 alkylamino, C1-C6 haloalkyl, C1-C6 alkylamino C1-C6 alkyl, C1-C6 alkoxy C1-C6 alkyl, piperidyl C1-C6 alkyl, and tetrahydropyranyl C1-C6 alkyl;

R₇ and R₈ are each independently selected from C1-C6 alkyl, or R₇ and R₈, together with the carbon atom attached thereto, form C3-C6 cycloalkyl or tetrahydropyranyl; and R₉ is selected from halogen, C1-C6 alkyl, C1-C6 alkoxy, and C1-C6 haloalkyl.

3. The kinase inhibitor compound according to claim 1, represented by Formula (Ia) or a pharmaceutically acceptable salt, solvate, ester, acid, or prodrug thereof, Formula (Ia)

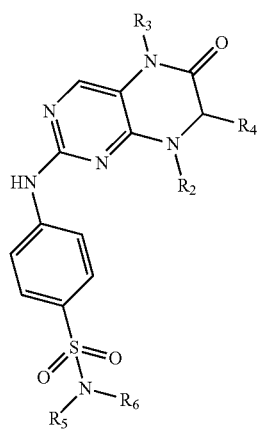

wherein R₂, R₃, R₄, R₅ and R₆ are defined as those in claim 1.

4. The kinase inhibitor compound according to claim 3, wherein R₂ and R₃ are methyl, R₄ is selected from C2-C6 spirocycloalkyl, phenyl optionally substituted with 1-3 R₉, and thienyl optionally substituted with 1-3 R₉; R₅ and R₆ are each hydrogen, and R₉ is selected from halogen, C1-C6 alkyl, and C1-C6 haloalkyl.

5. The kinase inhibitor compound according to claim 4, wherein R₉ is selected from fluorine, methyl and trifluoromethyl.

6. The kinase inhibitor compound according to claim 1, which is selected from the group consisting of the following compounds or a pharmaceutically acceptable salt thereof,

1

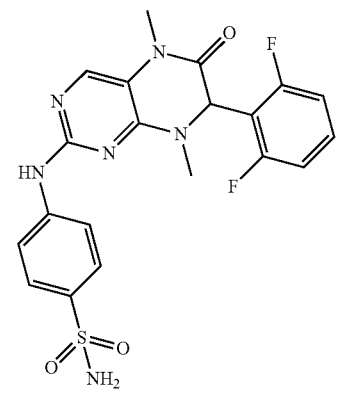

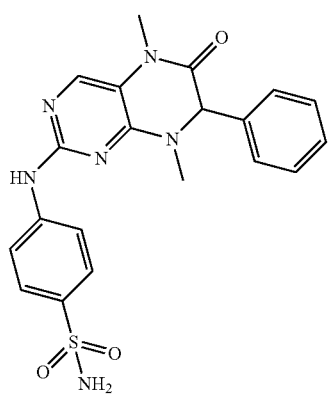 [SMILES: CN1C(=O)C(c2ccccc2)N(C)c2nc(Nc3ccc(S(N)(=O)=O)cc3)ncc21]
2
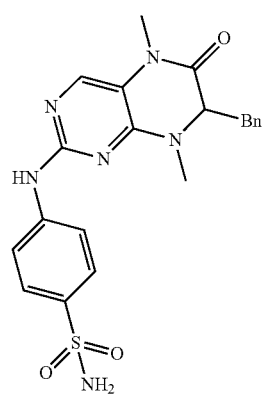 [SMILES: CN1C(=O)C(Cc2ccccc2)N(C)c2nc(Nc3ccc(S(N)(=O)=O)cc3)ncc21]
3
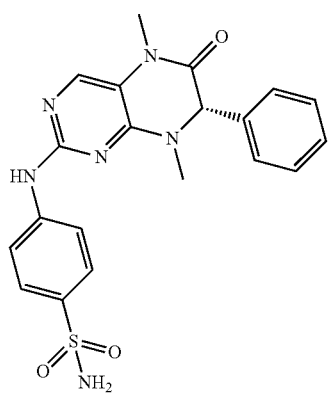 [SMILES: CN1C(=O)[C@H](c2ccccc2)N(C)c2nc(Nc3ccc(S(N)(=O)=O)cc3)ncc21]
4
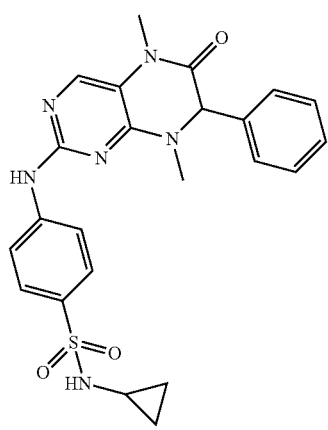 [SMILES: CN1C(=O)C(c2ccccc2)N(C)c2nc(Nc3ccc(S(=O)(=O)NC4CC4)cc3)ncc21]
6
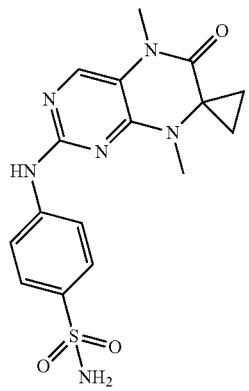 [SMILES: CN1C(=O)C2(CC2)N(C)c2nc(Nc3ccc(S(N)(=O)=O)cc3)ncc21]
7
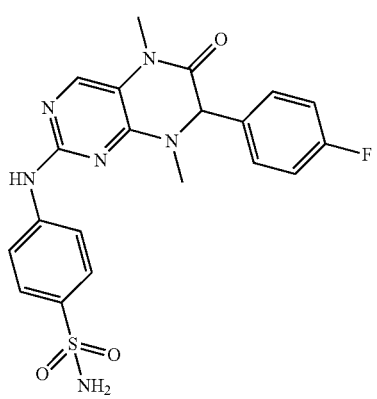 [SMILES: CN1C(=O)C(c2ccc(F)cc2)N(C)c2nc(Nc3ccc(S(N)(=O)=O)cc3)ncc21]
9
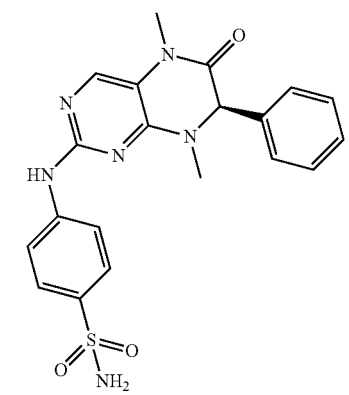 [SMILES: CN1C(=O)[C@@H](c2ccccc2)N(C)c2nc(Nc3ccc(S(N)(=O)=O)cc3)ncc21]
10
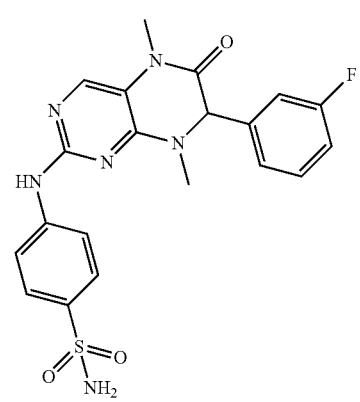 [SMILES: CN1C(=O)C(c2cccc(F)c2)N(C)c2nc(Nc3ccc(S(N)(=O)=O)cc3)ncc21]
11

12
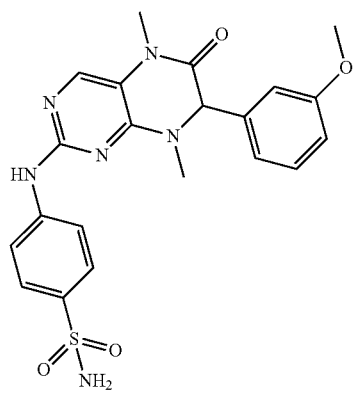 [SMILES: COc1cccc(C2C(=O)N(C)c3cnc(Nc4ccc(S(N)(=O)=O)cc4)nc3N2C)c1]
13
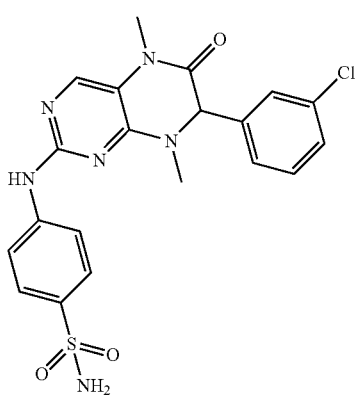 [SMILES: CN1C(=O)C(c2cccc(Cl)c2)N(C)c2nc(Nc3ccc(S(N)(=O)=O)cc3)ncc21]
14
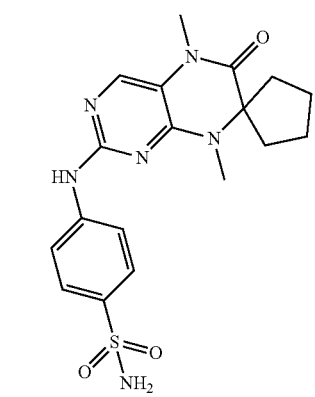
15
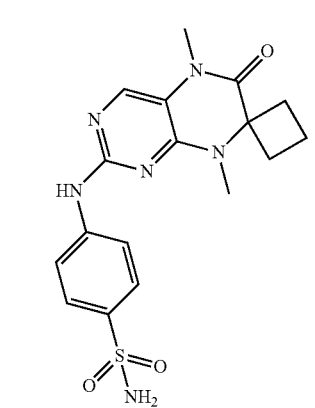 [SMILES: CN1C(=O)C2(CCC2)N(C)c2nc(Nc3ccc(S(N)(=O)=O)cc3)ncc21]
19
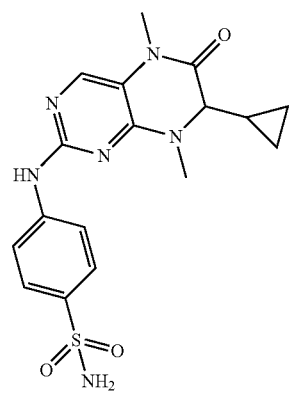 [SMILES: CN1C(=O)C(C2CC2)N(C)c2nc(Nc3ccc(S(N)(=O)=O)cc3)ncc21]
20
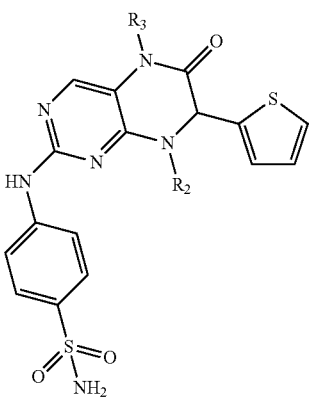
21
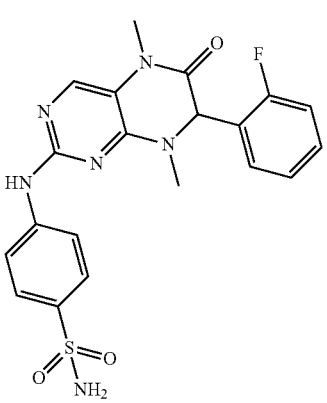
22
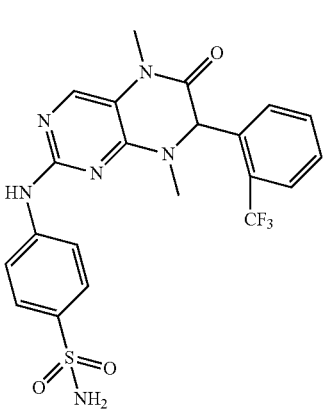

23
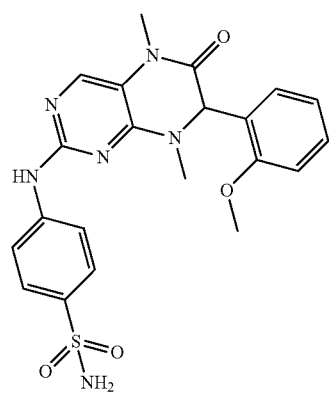 [SMILES: COc1ccccc1C1C(=O)N(C)c2cnc(Nc3ccc(S(N)(=O)=O)cc3)nc2N1C]
24
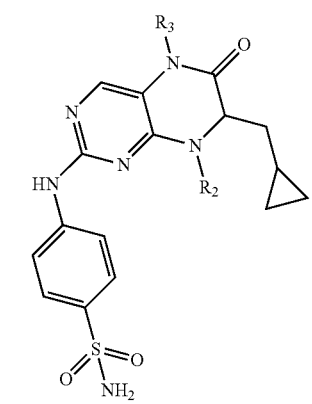
25
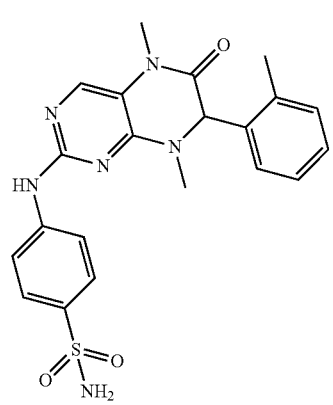
26
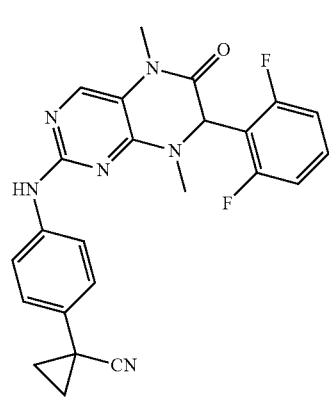 [SMILES: CN1C(=O)C(c2c(F)cccc2F)N(C)c2nc(Nc3ccc(C4(C#N)CC4)cc3)ncc21]
27
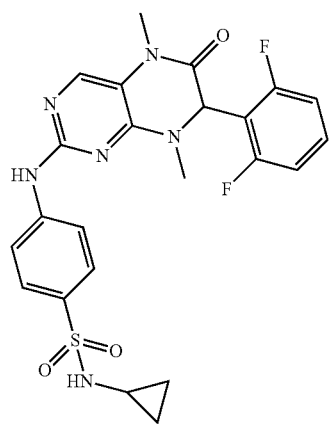 [SMILES: CN1C(=O)C(c2c(F)cccc2F)N(C)c2nc(Nc3ccc(S(=O)(=O)NC4CC4)cc3)ncc21]
28
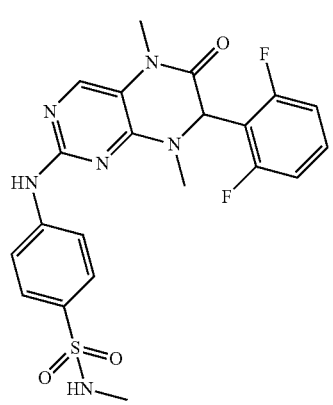 [SMILES: CNS(=O)(=O)c1ccc(Nc2ncc3c(n2)N(C)C(c2c(F)cccc2F)C(=O)N3C)cc1]
29
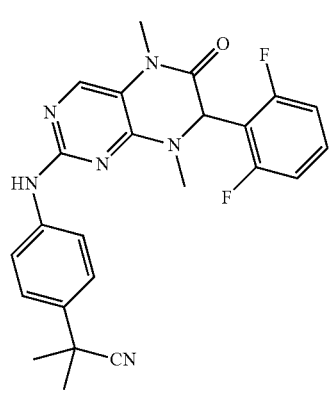
30
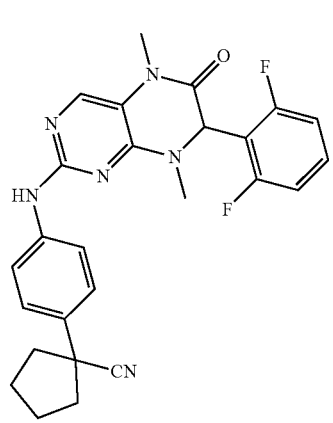 [SMILES: CN1C(=O)C(c2c(F)cccc2F)N(C)c2nc(Nc3ccc(C4(C#N)CCCC4)cc3)ncc21]

31
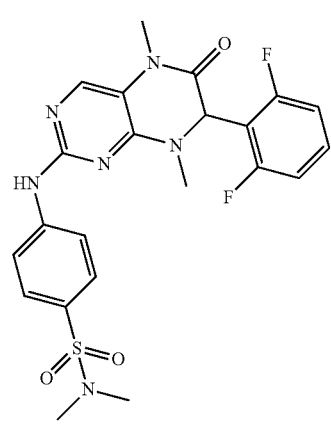 [SMILES: CN1C(=O)C(c2c(F)cccc2F)N(C)c2nc(Nc3ccc(S(=O)(=O)N(C)C)cc3)ncc21]
32
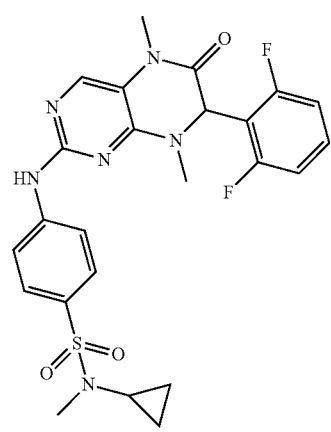 [SMILES: CN1C(=O)C(c2c(F)cccc2F)N(C)c2nc(Nc3ccc(S(=O)(=O)N(C)C4CC4)cc3)ncc21]
33
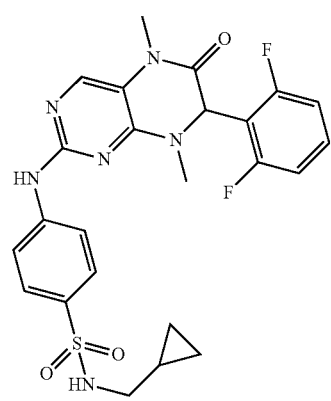 [SMILES: CN1C(=O)C(c2c(F)cccc2F)N(C)c2nc(Nc3ccc(S(=O)(=O)NCC4CC4)cc3)ncc21]
34
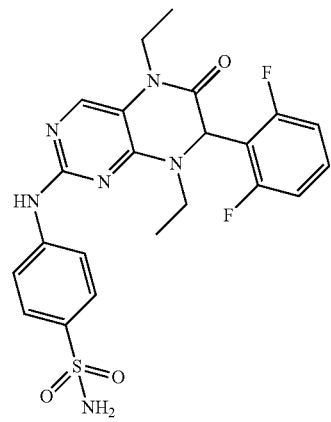 [SMILES: CCN1C(=O)C(c2c(F)cccc2F)N(CC)c2nc(Nc3ccc(S(N)(=O)=O)cc3)ncc21]
35
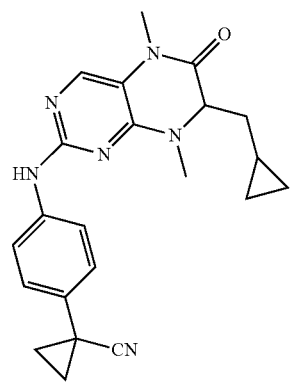 [SMILES: CN1C(=O)C(CC2CC2)N(C)c2nc(Nc3ccc(C4(C#N)CC4)cc3)ncc21]
36
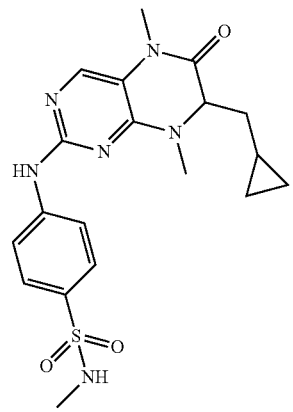 [SMILES: CNS(=O)(=O)c1ccc(Nc2ncc3c(n2)N(C)C(CC2CC2)C(=O)N3C)cc1]
37
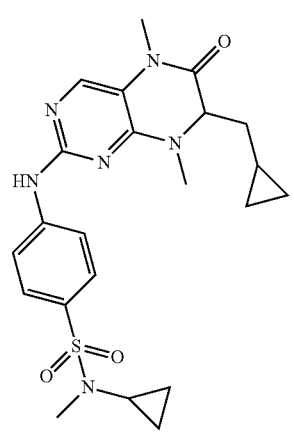 [SMILES: CN1C(=O)C(CC2CC2)N(C)c2nc(Nc3ccc(S(=O)(=O)N(C)C4CC4)cc3)ncc21]

38
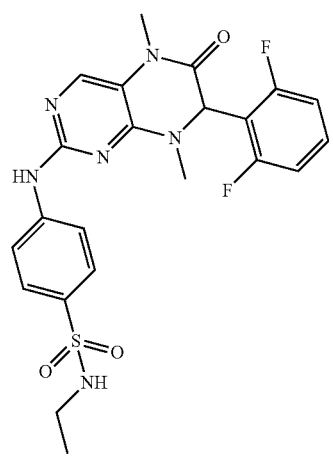
39
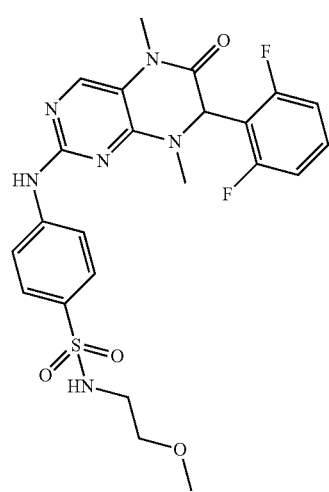 [SMILES: COCCNS(=O)(=O)c1ccc(Nc2ncc3c(n2)N(C)C(c2c(F)cccc2F)C(=O)N3C)cc1]
40
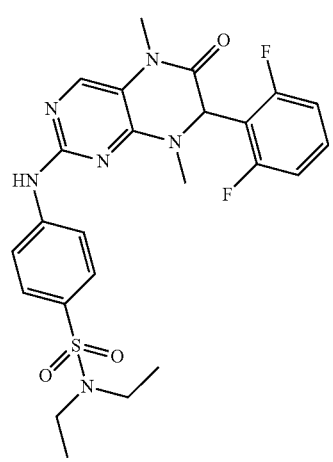 [SMILES: CCN(CC)S(=O)(=O)c1ccc(Nc2ncc3c(n2)N(C)C(c2c(F)cccc2F)C(=O)N3C)cc1]
41
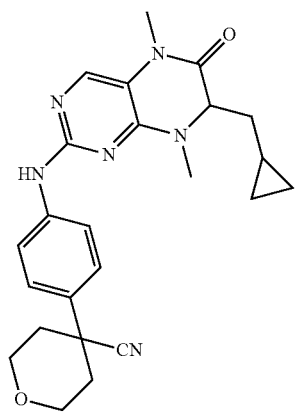 [SMILES: CN1C(=O)C(CC2CC2)N(C)c2nc(Nc3ccc(C4(C#N)CCOCC4)cc3)ncc21]
42
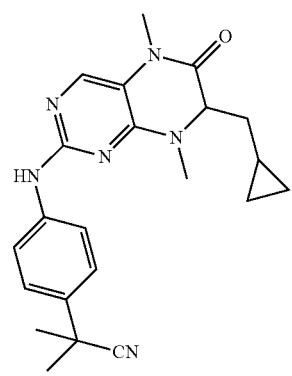 [SMILES: CN1C(=O)C(CC2CC2)N(C)c2nc(Nc3ccc(C(C)(C)C#N)cc3)ncc21]
43
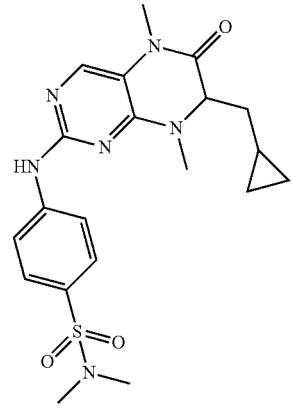 [SMILES: CN1C(=O)C(CC2CC2)N(C)c2nc(Nc3ccc(S(=O)(=O)N(C)C)cc3)ncc21]
44
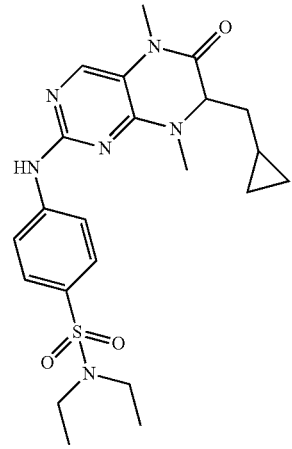 [SMILES: CCN(CC)S(=O)(=O)c1ccc(Nc2ncc3c(n2)N(C)C(CC2CC2)C(=O)N3C)cc1]

45
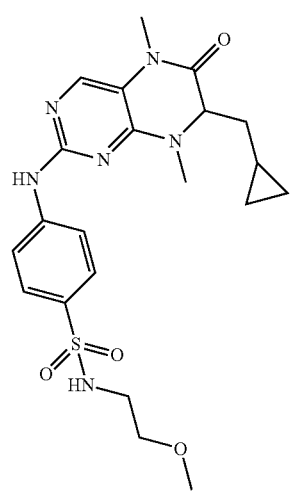 [SMILES: COCCNS(=O)(=O)c1ccc(Nc2ncc3c(n2)N(C)C(CC2CC2)C(=O)N3C)cc1]
46
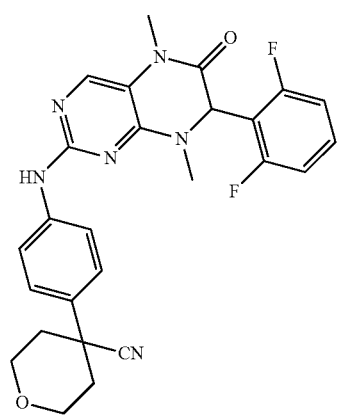 [SMILES: CN1C(=O)C(c2c(F)cccc2F)N(C)c2nc(Nc3ccc(C4(C#N)CCOCC4)cc3)ncc21]
47
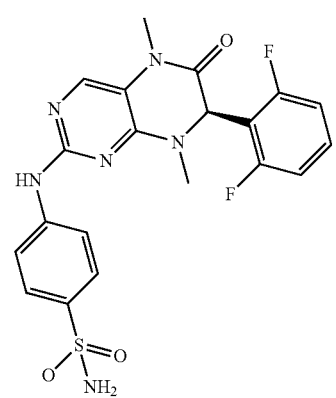 [SMILES: CN1C(=O)[C@@H](c2c(F)cccc2F)N(C)c2nc(Nc3ccc(S(N)(=O)=O)cc3)ncc21]
48
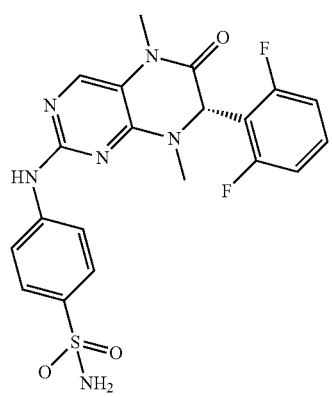 [SMILES: CN1C(=O)[C@H](c2c(F)cccc2F)N(C)c2nc(Nc3ccc(S(N)(=O)=O)cc3)ncc21]
49
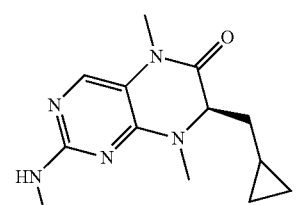
50
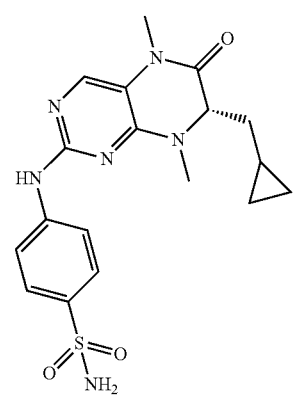
51
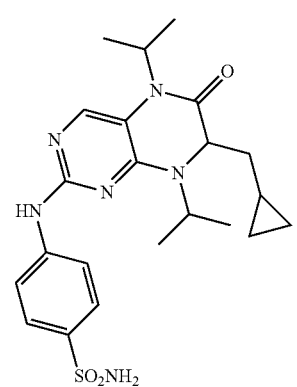 [SMILES: CC(C)N1C(=O)C(CC2CC2)N(C(C)C)c2nc(Nc3ccc(S(N)(=O)=O)cc3)ncc21]

52
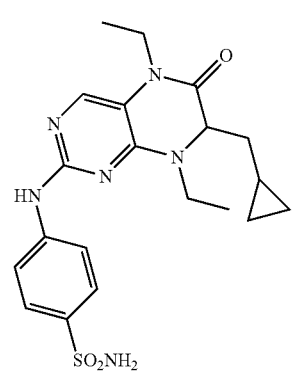 [SMILES: CCN1C(=O)C(CC2CC2)N(CC)c2nc(Nc3ccc(S(N)(=O)=O)cc3)ncc21]
53
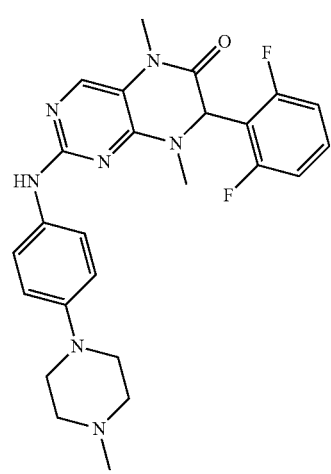 [SMILES: CN1CCN(c2ccc(Nc3ncc4c(n3)N(C)C(c3c(F)cccc3F)C(=O)N4C)cc2)CC1]
54
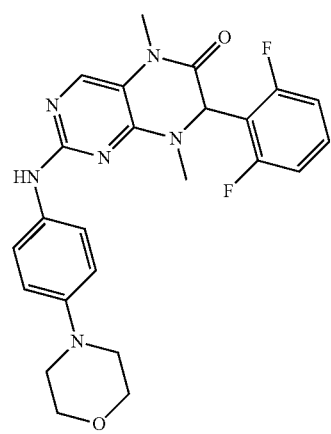 [SMILES: CN1C(=O)C(c2c(F)cccc2F)N(C)c2nc(Nc3ccc(N4CCOCC4)cc3)ncc21]
55
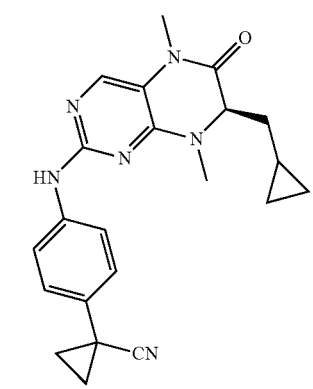 [SMILES: CN1C(=O)[C@@H](CC2CC2)N(C)c2nc(Nc3ccc(C4(C#N)CC4)cc3)ncc21]
56
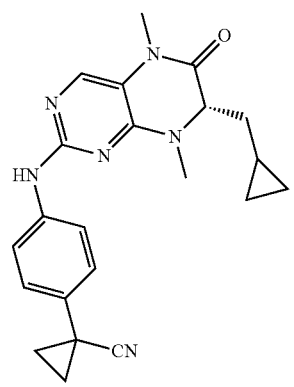 [SMILES: CN1C(=O)[C@H](CC2CC2)N(C)c2nc(Nc3ccc(C4(C#N)CC4)cc3)ncc21]
57
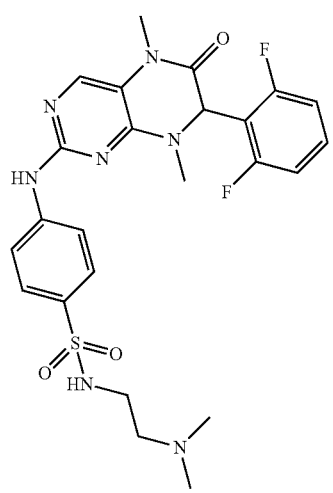 [SMILES: CN(C)CCNS(=O)(=O)c1ccc(Nc2ncc3c(n2)N(C)C(c2c(F)cccc2F)C(=O)N3C)cc1]
58
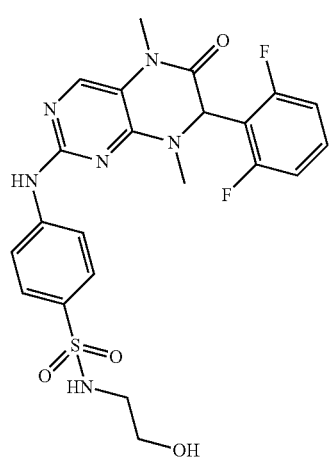 [SMILES: CN1C(=O)C(c2c(F)cccc2F)N(C)c2nc(Nc3ccc(S(=O)(=O)NCCO)cc3)ncc21]

59
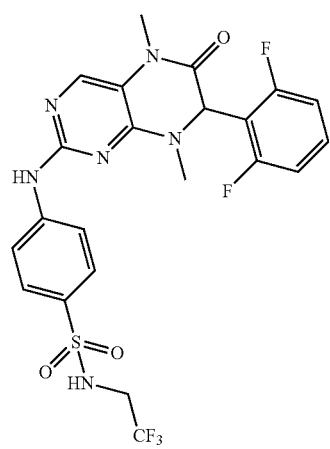
60
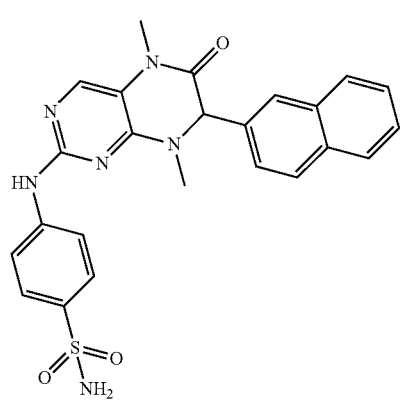 [SMILES: CN1C(=O)C(c2ccc3ccccc3c2)N(C)c2nc(Nc3ccc(S(N)(=O)=O)cc3)ncc21]
61
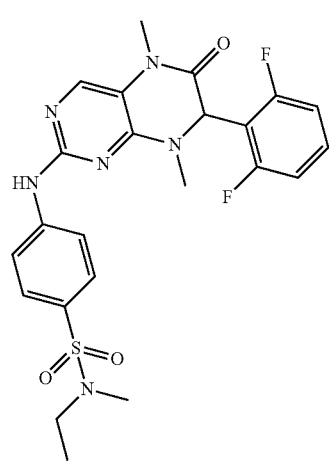 [SMILES: CCN(C)S(=O)(=O)c1ccc(Nc2ncc3c(n2)N(C)C(c2c(F)cccc2F)C(=O)N3C)cc1]
62
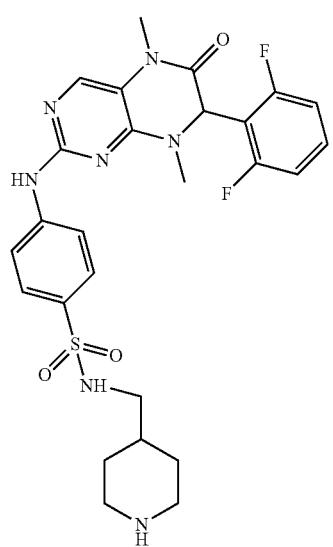 [SMILES: CN1C(=O)C(c2c(F)cccc2F)N(C)c2nc(Nc3ccc(S(=O)(=O)NCC4CCNCC4)cc3)ncc21]
63
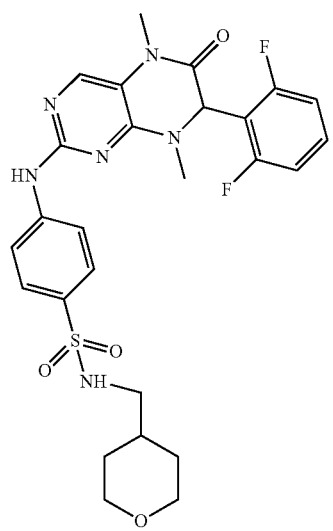 [SMILES: CN1C(=O)C(c2c(F)cccc2F)N(C)c2nc(Nc3ccc(S(=O)(=O)NCC4CCOCC4)cc3)ncc21]
64
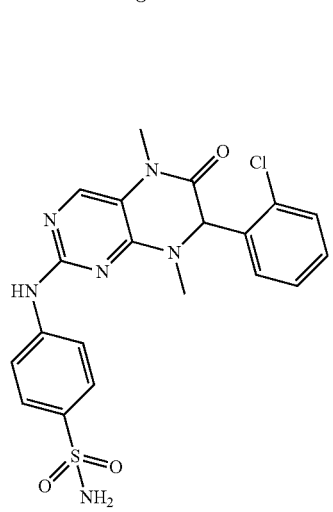

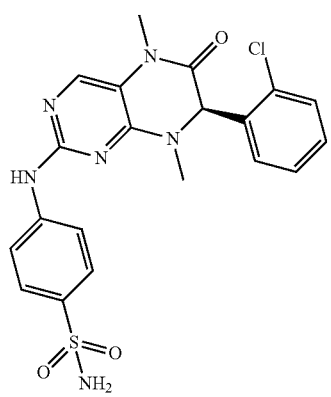 [SMILES: CN1C(=O)[C@@H](c2ccccc2Cl)N(C)c2nc(Nc3ccc(S(N)(=O)=O)cc3)ncc21]
65
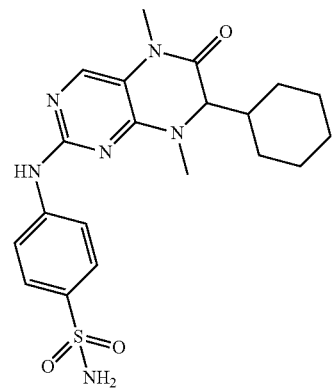
66
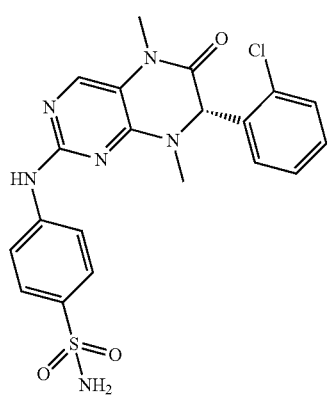 [SMILES: CN1C(=O)[C@H](c2ccccc2Cl)N(C)c2nc(Nc3ccc(S(N)(=O)=O)cc3)ncc21]
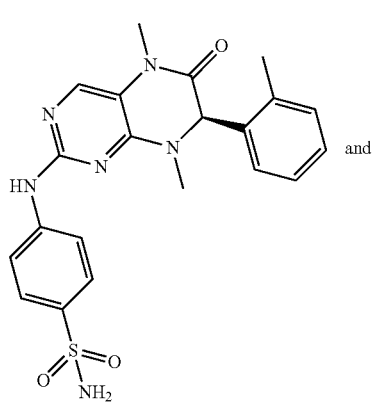 and
67
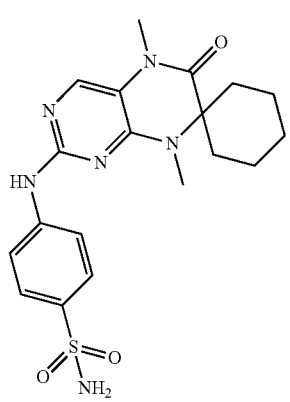 [SMILES: CN1C(=O)C2(CCCCC2)N(C)c2nc(Nc3ccc(S(N)(=O)=O)cc3)ncc21]
68
69
70
7. A pharmaceutical composition comprising the kinase inhibitor compound according to claim 1, a pharmaceutically acceptable carrier or excipient, and optionally other therapeutic agents.
* * * * *